United States Patent [19]

Duffy et al.

[11] 4,408,616

[45] Oct. 11, 1983

[54] BRAIN ELECTRICAL ACTIVITY MAPPING

[75] Inventors: Frank H. Duffy, Brookline, Mass.; Norman D. Culver, Spotswood, N.J.

[73] Assignee: The Children's Medical Center Corporation, Boston, Mass.

[21] Appl. No.: 264,043

[22] Filed: May 15, 1981

[51] Int. Cl.³ .............................................. A61B 5/04
[52] U.S. Cl. ................................................... 128/731
[58] Field of Search ............................... 128/731–733, 128/905

[56] References Cited

U.S. PATENT DOCUMENTS

| | | | |
|---|---|---|---|
| 2,928,189 | 3/1960 | Molner et al. | 35/22 |
| 3,696,808 | 10/1972 | Roy et al. | 128/2.1 B |
| 3,705,297 | 12/1972 | John | 235/150.53 |
| 3,706,308 | 12/1972 | John et al. | 128/2.06 R |
| 3,707,147 | 12/1972 | Sellers | 128/2.06 G |
| 3,717,141 | 2/1973 | Krohn et al. | 128/2.66 R |
| 3,780,724 | 12/1973 | John | 128/2.1 B |
| 3,799,146 | 3/1974 | John et al. | 128/2.1 B |
| 3,837,331 | 9/1974 | Ross | 128/732 X |
| 3,901,215 | 8/1975 | John | 128/2.1 B |
| 3,958,563 | 5/1976 | Fernandez et al. | 128/731 |
| 4,094,307 | 6/1978 | Young | 128/2.1 B |
| 4,171,696 | 10/1979 | John | 128/731 |
| 4,201,224 | 5/1980 | John | 128/731 |
| 4,214,591 | 7/1980 | Sato et al. | 128/731 |

OTHER PUBLICATIONS

Duffy et al.; Significance Probability Mapping: An Aid in the Topographic Analysis of Brain Electrical Activity; EEG and Clin. and Neurophysiology, 1981; pp. 1–8.
Duffy et al.; "Quantification of Focal Abnormalities in Beam Data by Grid Sector Analysis".
Duffy et al.; "Dyslexia: Automated Diagnosis of Computerized Classif. of Brain Electrical Activity"; Annals of Neur., vol. 7, No. 5, 5–1980, pp. 421–428.
Duffy et al.; "Dyslexia: Regional Diff. in Brain Electrical Activity by Topographic Mapping"; Annals of Neur., vol. 7, No. 5, 5–1980, pp. 412–420.
Ueno et al., Topographic Computer Display of Abnormal EEG Activities in Patients with CNS Diseases, Memoirs of the Faculty of Engineering, Kyushu University, vol. 34, No. 3, (Feb., 1975) pp. 195–209.
Marguerite Zientara (CW Staff) Multiple Personalities 'Mapped' by Computer, Computer World Publication, Jan. 24, 1983, p. 14.
Duffy et al., "Brain Electrical Activity Mapping (BEAM): A Method for Extending the Clinical Utility of EEG and Evoked Potential Data," Annals of Neurology, vol. 5, No. 4 (Apr., 1979) pp. 309–321.

Primary Examiner—Lee S. Cohen
Assistant Examiner—Angela D. Sykes

[57] ABSTRACT

Topographic displays of brain electrical activity are produced from matrices of data derived from evoked potential (EP) and steady-state responses of skull transducers. In different aspects, EP responses are displayed at a variable frame rate, the rate of data sampling is sufficient to capture rapid transient events, difference matrices are derived as the difference between matrices corresponding to two different brain conditions, the baseline of the EP responses is zeroed based on the average prestimulus response, and the steady-state response is analyzed by Fourier transforms. In other aspects, statistical comparison matrices representing statistical differences between corresponding elements in two matrices are generated, a coefficient-of-variance matrix is generated, additional display matrices are temporally interpolated, response waveforms are previewed and tagged for elimination from further processing, the topographic maps are displayed on a video monitor with appropriate scaling of the data to the tones of the display, and additional display points are interpolated between the measured data points for display.

82 Claims, 32 Drawing Figures

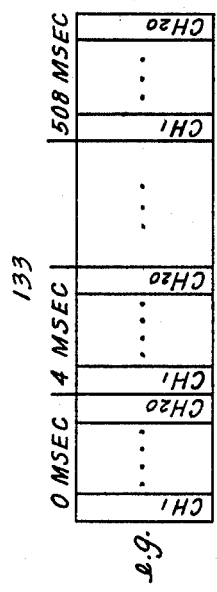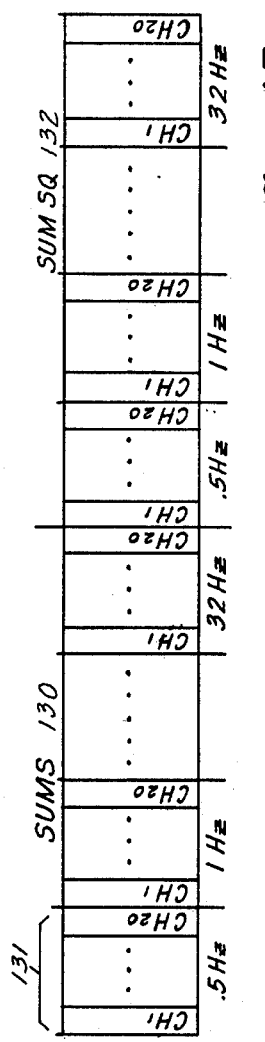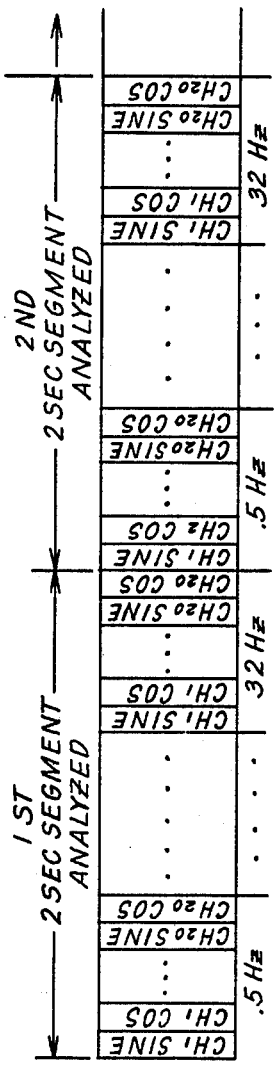

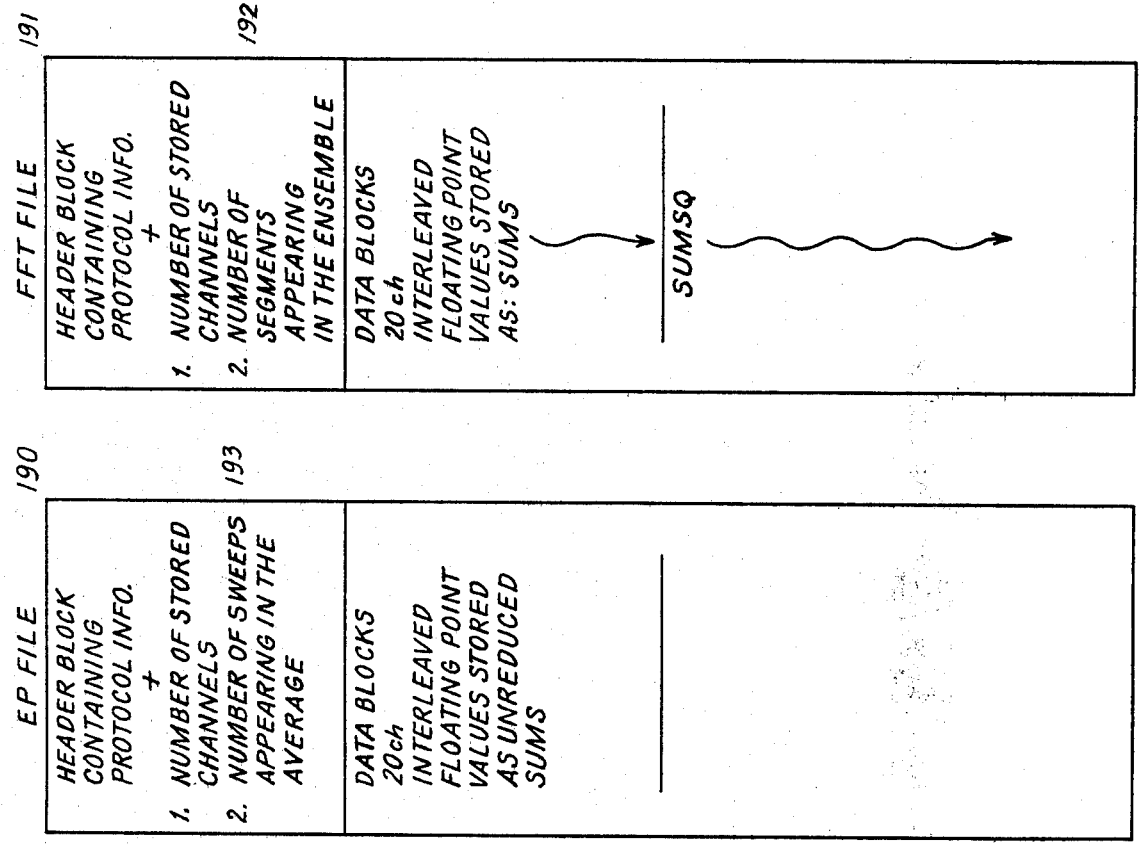

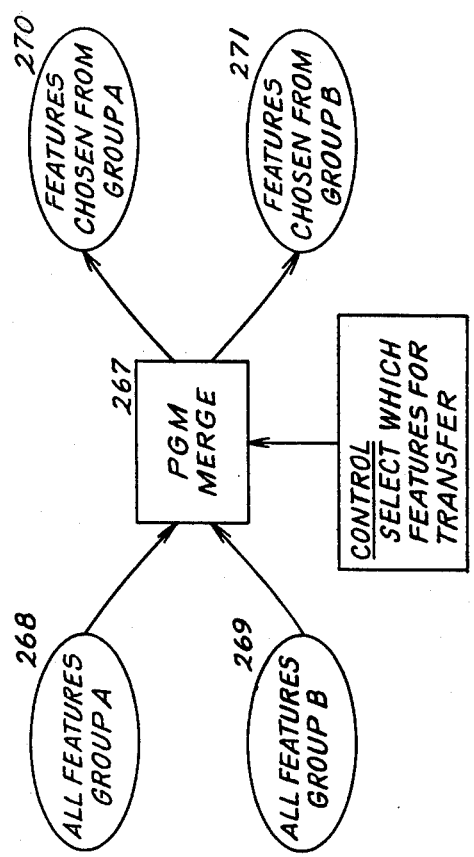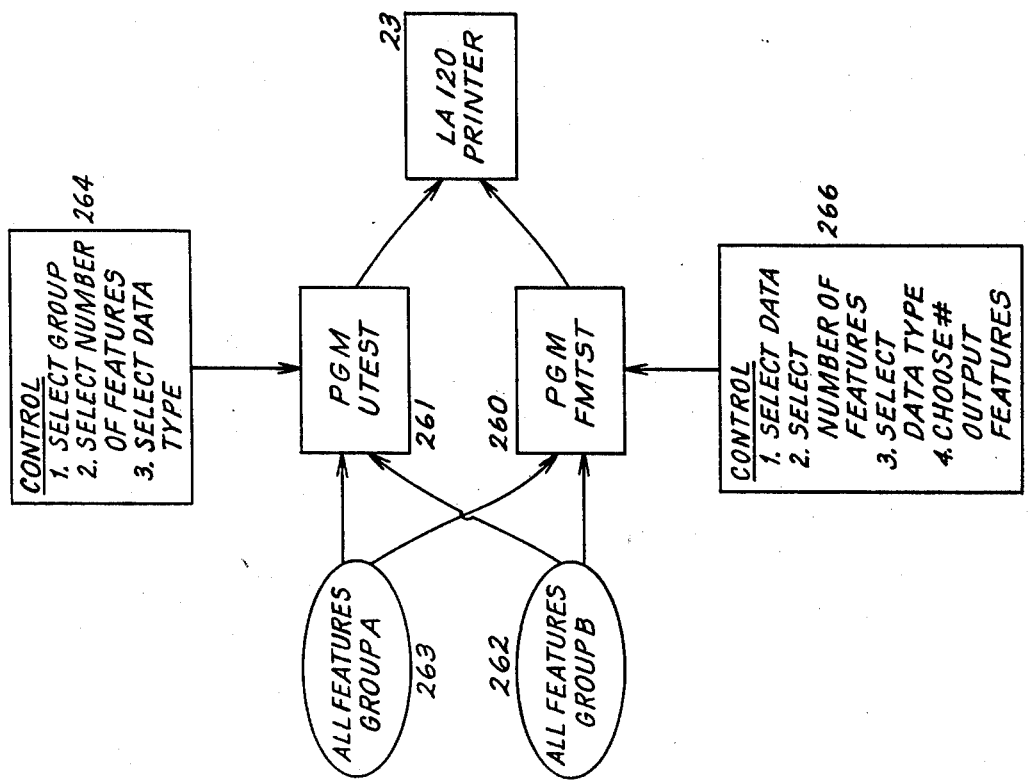
Fig 28

BRAIN ELECTRICAL ACTIVITY MAPPING

The invention described herein was made in the course of work under a grant or award from the Department of Health and Human Services.

BACKGROUND OF THE INVENTION

This invention relates to analysis of brain electrical activity and diagnosis of brain disorders.

Traditional electro-encephalographic (EEG) techniques of analyzing brain electrical activity to diagnose brain dysfunction require the skilled neurophysiologist to observe and distinguish time and frequency related characteristics of many channels of voltage waveforms derived from an individual's brain and to determine, largely from memory, differences between that individual's waveforms and waveforms characteristic of a normalized population. The process necessarily fails to take account of many subtle but potentially useful pieces of information contained in the analyzed data.

Signal averaged sensory evoked potential (EP) transient responses have also been used as a source for brain electrical activity analysis, but large amounts of useful information contained in such transient response waveforms have traditionally been disregarded because of the difficulty of visualizing the inter-relationship over time of many channels of such information.

SUMMARY OF THE INVENTION

The invention features, in one aspect, displaying time sequences of topographic maps at a variable frame rate. In preferred embodiments, the rate can be selected to display protions of the EP response immediately following the stimulus at a slower rate than later portions; and in preferred embodiments the rate can be varied logarithmically. The variation of display rate permits the operator to give more emphasis to matrices which contain relatively more information, such as the earlier EP response matrices.

In another aspect, the invention features generating topographic displays of information on electrical activity of the brain produced at a plurality of transducers on the skull; generating a time sequence of matrices of electrical activity at successive points in time sufficient in number to capture the onset of a rapid transient event; and displaying the matrices as topographic maps in time sequence at a variable rate. In preferred embodiments, the processor is capable of generating 200 or more matrices for each second of real time. The ability to capture a large number of matrices in a short period of time permits the observation of short-term events such as epileptic spikes.

In another aspect, the invention features generating topographic displays of information on brain electrical activity produced at a plurality of skull transducers; storing the electrical activity of such transducers for two different brain conditions; generating matrices of elements representing electrical activity in the two conditions; forming a difference matrix between corresponding elements of the two matrices; and displaying the difference matrix as a topographic map. In preferred embodiments, the two brain conditions are attained by the use of a patterned light stimulus and a non-patterned light stimulus. The ability to form and display difference matrix enables the operator to identify parts of the brain involved in particular brain states or evoked responses.

In another aspect, the invention features generating topographic displays of information on brain electrical activity produced at a plurality of skull transducers; repeatedly triggering EP responses at the transducers, including pre-stimulus and post-stimulus responses; averaging the responses; setting as a baseline the mean level of the pre-stimulus response; generating matrices from such responses; and displaying topographic maps of the matrices. In preferred embodiments the time of occurrence of each stimulus is stored and the response is divided into pre-stimulus and post-stimulus periods; the matrices generated are a set of time-sequenced frames during the response and are displayed as a sequence of topographic maps; the sequence can be displayed as an endless sequence of maps; the averaging process can be performed using digital words added into summing buffers; and the sampling, storing, response averaging, baseline calculation and subtraction can all be performed digitally; averaging of the pre-stimulus baseline can exclude selected portions of the response; the response can be reviewed to determine the appropriateness of the baseline; there can be calculated the $V_{RMS}$ of the average pre-stimulus and post-stimulus responses and the $V_{RMS}$ can be displayed with the responses, so that the user can determine whether the noise level for any transducer is unacceptably large; the operator can manually adjust the baseline up or down; high-frequency components can be filtered from the post-stimulus response by multipoint interpolation; and the baseline calculation can be repeated until the results are satisfactory. In general, these various features permit the operator to assemble, modify and adjust to an accurate zero level a set of EP responses so that the ultimate topographic display will be accurate and useful. The display of a time-sequence of frames permits the operator to visualize the movement of brain activity in the course of an EP response over the skull. The proper setting at the baseline improves the utility of each response when used in a topographic display, since the relative levels of response at different transducers is more accurately portrayed.

In another aspect, the invention features filtering to remove from the EEG responses frequency components outside the prominent frequency bands of electrical activity; determining, for each transducer, the Fourier transforms and the spectral energy in selected frequency bands, during a period when the brain activity remains in the same state; and processing the results into display matrices for the selected frequency bands. In preferred embodiments, the brain activity can be sampled, stored and Fourier transformed digitally; the filters can remove frequency components below 0.5 Hz and about 50 Hz; the samples can be taken at least 3 times as frequently as the highest frequency in the prominent frequency bands, and particularly at 4 to 5 times that highest frequency; the Fourier analysis can be limited to a period between marked starting and stopping points; the period during which electrical activity is sampled can be limited to avoid interruptions in the subject's brain state, and particularly can be limited to two second sampling periods; the number of samples can be between 20 and 2000; and the frequency bands analyzed can comprise the alpha, beta, delta and theta bands. Removal of irrelevant frequency bands, sampling at high rate, and limiting the sampling period all enable the operator to obtain accurate spectral analyses with minimum interference. The ability to analyze specific frequency bands of interest enables the operator to review information which effectively corresponds to the electrical activity of the brain in various states.

In another aspect, the invention also features generating a statistical comparison matrix from two matrices, each element of the statistical comparison matrix representing a statistical difference between the corresponding elements in the two matrices; and displaying the statistical comparison matrix as a topographic map. In preferred embodiments, the statistical comparison matrix can be interpolated into a display matrix having additional display points; the statistical comparison can be made between two expanded matrices rather than between two unexpanded matrices; the statistical comparison can be a t-statistic analysis, or a z-statistic analysis; and quantitative features useful for diagnosis can be determined from regions of the maps. The ability to perform and topographically display statistical differences between groups and between an individual and a group offers a versatile and effective tool for visualizing brain areas which are connected to particular brain dysfunctions or to particular brain activities, and for neurophysiological diagnosis and research.

In another aspect, the invention also features generating a coefficient-of-variance matrix, each element of which represents the normalized standard deviation at one skull location; and displaying the coefficient-of-variance as a topographic map.

In another aspect, the invention also features temporally interpolating matrices which represent the response at time instants between other matrices; and displaying said interpolated matrices. The temporal interpolation provides a smoother visual transition between the original frames when a time-sequenced display is presented.

In another aspect, the invention also features previewing waveforms and tagging a waveform to indicate whether it should be used in later processing, eliminating a response from further processing, automatically eliminating a response from further processing if a portion of the response exceeds a predetermined threshhold, smoothing a response by eliminating undesired high-frequency components, for adjusting the zero baseline of a response, eliminating selected portions of a response from further processing, and displaying in numerical form the value of a response at a point in time selected by the operator. These waveform quality control procedures enable the operator to improve the quality and accuracy of the topographic displays.

In another aspect, the invention features generating a topographic display of information on the electrical activity produced at a plurality of skull transducers; sampling and storing the information as a series of matrices; viewing the data as a waveform; adjusting or eliminating portions of the data, processing the matrices into processed matrices; interpolating to expand the matrices for viewing; and displaying the matrices as topographic maps in a grey tone scale. In preferred embodiments, the data matrices, processed matrices and expanded matrices can be tagged and stored for later recall and processing; and the data matrix elements can be calibrated to stored calibration signals by calculating a DC offset and gain component for each transducer. The ability to store display matrices for later use enables the operator to accumulate a series of significant matrices derived from diagnostic or research work. The calibration assures that the topographic displays will be accurate.

In another aspect, the invention features generating a topographic display of electrical activity of the brain produced from a plurality of electrical transducers on the skull; generating matrices of elements representing the electrical activity at different points; using a video monitor to display said matrices, each element of which is represented by a discrete point having a gray tone of color lying within a range of gray tones; and scaling the elements to the tones. In preferred embodiments, scaling can be performed so that all elements are linearly interpolated between the maximum gray tone and the minimum gray tone, or between the maximum gray tone and a "zero" gray tone, or to an operator supplied gray one, or so that certain display elements are excluded from the scaling, or that elements falling outside the available gray tone range are assigned to the closest gray tone; the gray tones can be generated in two colors, which can be complementary colors, representing values on either side of a zero tone, the zero tone being an absence of color; the scaling can be performed either on a matrix by matrix basis, or for all matrices taken together; the data which forms the input to the scaling operation can be previewed to by selected lab for exclusion from the scaling operation. The ability to scale the display data to a range of gray tones in a variety of ways improves the utility and visual effect of the display. The variety of scaling options is suitable for the variety of data which may be displayed. The ability to eliminate very large values from the scaling operation assures the most effective scaling for a given set of data.

In another aspect, the invention features normalizing display matrix elements to a selected value which can be assigned to a selected gray tone for purposes of scaling. In preferred embodiments, the normalization can be to a matrix element representing a particular vertex transducer on the skull, or to the root mean square value of the background activity at the transducer being normalized, or to the average root mean square value of the background activity at all skull locations; normalization can be done in connection with apparatus for topographically displaying a sequence of matrices representing averaged EP responses to repeatedly provided stimuli; normalization can be done in connection with apparatus for displaying spectral band matrices derived by Fourier transform analysis of the electrical activity, the normalization being of each element of each spectral band to the total spectral energy at the corresponding transducer on the average total spectral energy at all transducers. The ability to normalize display elements improves the operator's ability to compare different sets of data by normalizing them to the same value.

In preferred embodiments, the invention features interpolating to form additional matrix elements between the transducer points; the interpolation can be three-point interpolation, particularly three-point linear interpolation to the values of the three closest transducers; the number of transducers can be in the range of 10 to 200; and the number of picture elements is at least 5 times the number of transducers. The expansion of a matrix of a small number of points to a display matrix of a large number of points significantly improves the smoothness, readability and utility of the resulting topographic displays.

BRIEF DESCRIPTION OF THE DRAWINGS

FIG. 14 is a data file format diagram of signal averaged EP data.

FIG. 15 is a data file format diagram of FFT ensemble data.

FIG. 16 is a data file format diagram of individual FFT data.

FIG. 17 is a data file format diagram of an EP file.

FIG. 18 is a data file format diagram of an FFT file.

FIG. 26 is a data file format diagram of a saved frame file.

FIG. 28 is a block diagram of the TICAS feature selection and evaluation operation.

DESCRIPTION OF THE PREFERRED EMBODIMENT

We now turn to a description of the preferred embodiment.

System Organization and Software

Figure 1:
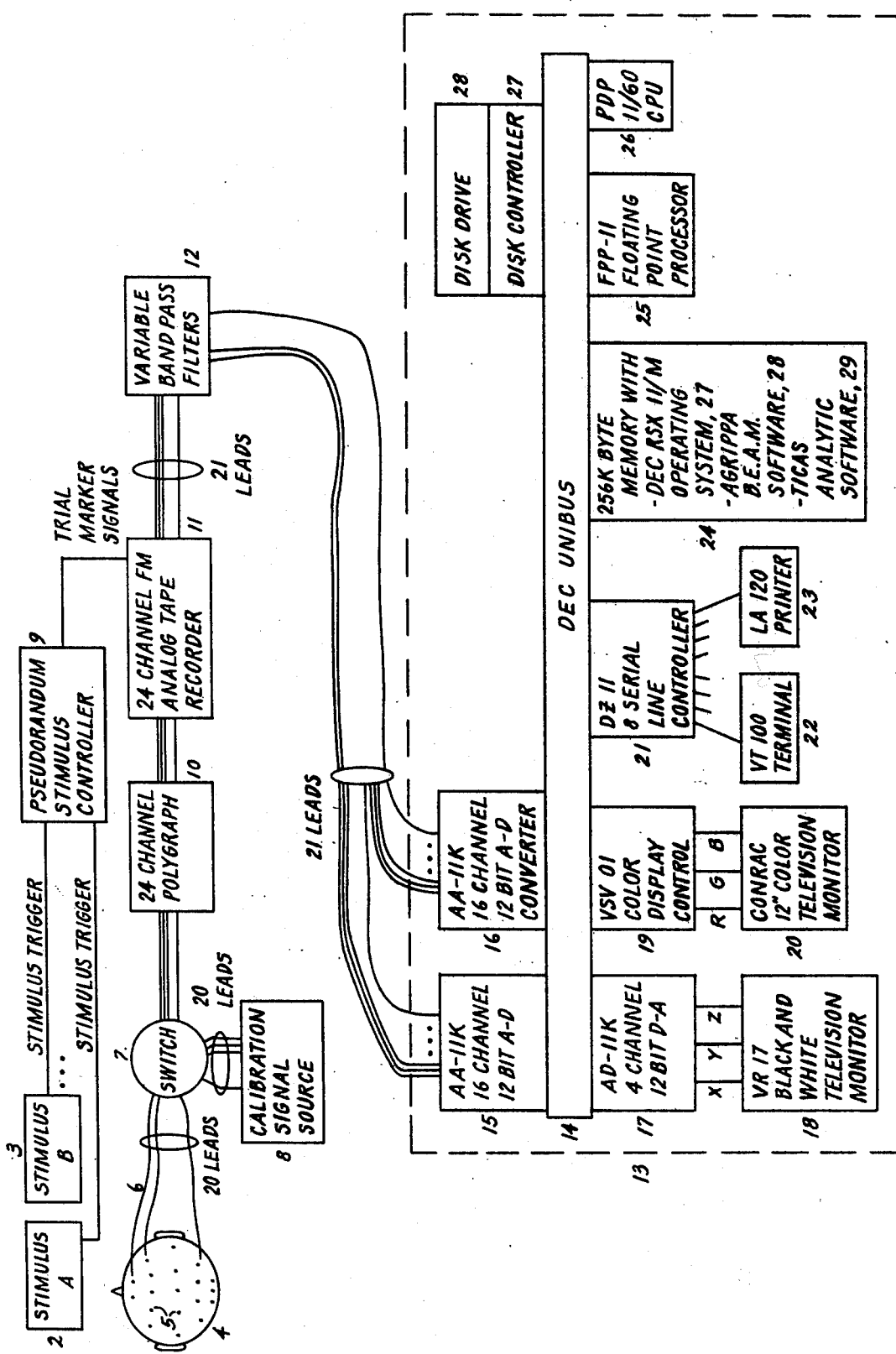
FIG. 1 is a block diagram of the BEAM system.

FIG. 1 illustrates the components of a brain electrical activity mapping system. Twenty electrodes 5 (e.g., Grass gold cup) are attached to subject's skull 4 in a conventional international 10-20 format. Twenty leads 6 from electrodes 5 are connected through switch 7 to conventional 24-channel polygraph 10 (e.g., Grass 8-24D), which contains parallel variable gain differential amplifiers and strip chart recorders. Calibration signal source 8, an A.C. generator, is also connected through switch 7 to polygraph 10. Stimulus A 2 (e.g., Grass Model PS1 strobe light) and stimulus B 3 (e.g., click generator) present stimuli to the subject under the control of pseudorandom stimulus controller 9, which also provides pre-stimulus and stimulus trial marker signals (5 volt spikes) of opposite polarity to one of the input channels to 24-channel FM analog tape recorder 11 (e.g., Honeywell 5600E). In other embodiments, recorder 11 is eliminated and polygraph 10 is connected directly to filter 12 for real-time loading of data. The 21 active outputs of recorder 11 are connected to the inputs of 21 parallel variable band pass filters 12 (e.g., Butterworth filters; EEG Associates Mark 4×24) having variable gain controls. The 21 outputs of filters 12 are connected to 21 of the input terminals of two 16-channel, 12-bit analog-to-digital converters 15, 16 (Digital Equipment Corporation AA-11K), which comprise part of digital computer 13 (Digital Equipment Corporation PDP 11/60). Analog-to-digital converters 15, 16 are attached to data bus 14 (Digital Equipment Corporation Unibus). Also attached to data bus 14 are 4-channel, 12-bit digital-to-analog converter 17 (Digital Equipment Corporation AD-11K) whose three outputs control black and white television monitor 18 (Digital Equipment Corporation VR 17) for waveform displays; color display control 19 (Digital Equipment Corporation VSV 01) whose three outputs control 12" color television monitor 20 (CONRAC) for topographic displays; 8 serial line controller 24 (Digital Equipment Corporation DZ 11) two outputs of which control interactive keyboard and video character display terminal 22 (Digital Equipment Corporation VT 100) and printer 23 (Digital Equipment Corporation LA 120); 256K byte memory 24 containing operating system software 27 (Digital Equipment Corporation RSX 11/M), BEAM software 28 (Agrippa Data Systems), and analytic software 29 (TICAS; University of Arizona); floating point processor 25 (Digital Equipment Corporation FPP-11); central processing unit 26 (Digital Equipment Corporation PDP 11/60); and disk controller 27 controlling at least one disk drive 28.

Software Description

Figure 2:
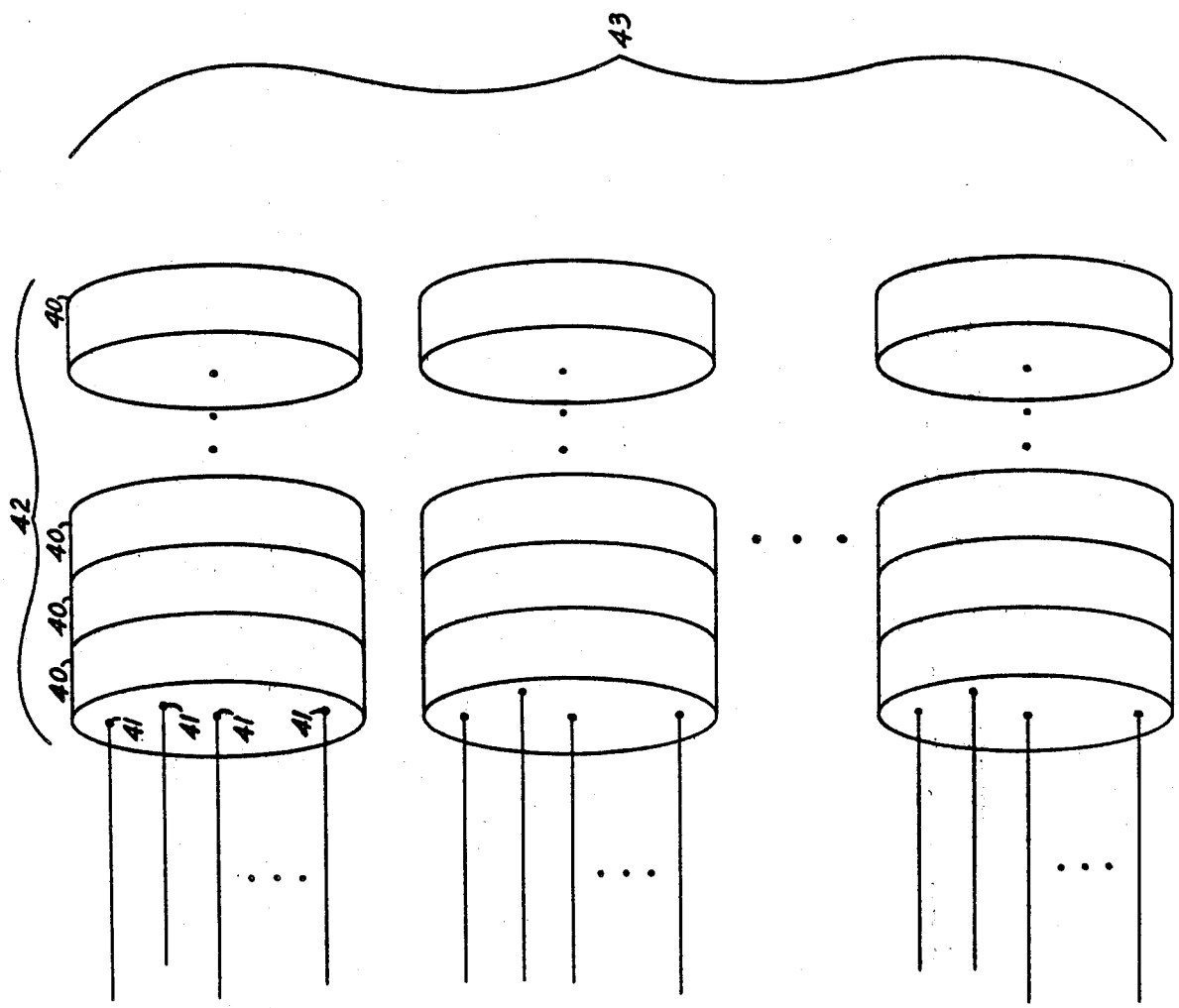
FIG. 2 is a representation of the organization of samples of data in the brain electrical activity mapping system.
Figure 3:
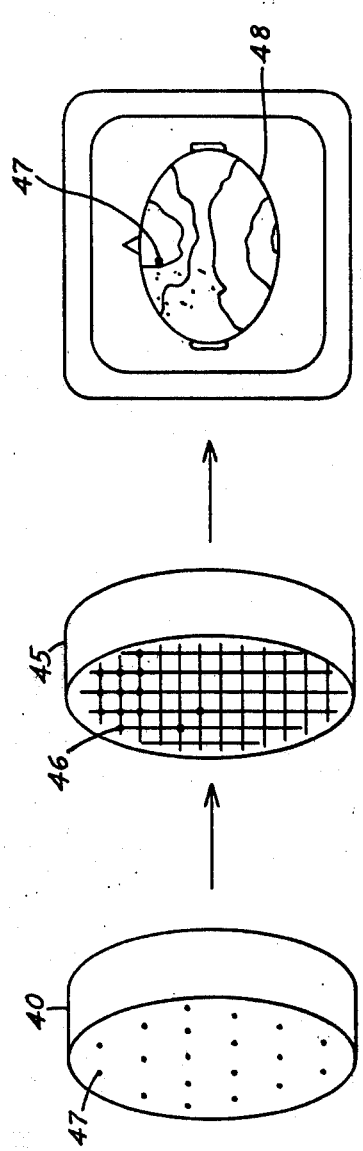
FIG. 3 is a representation of the formation of a topographic display from a frame of data in the brain electrical activity mapping system.

In general, the brain electrical activity mapping system creates color topographic displays reflecting brain electrical activity using, as input, continuous electrical waveforms recorded from a number of points on the skull. The color topographic displays consist of discrete matrices of a large number of display points (also called pixels), each of which has a color or intensity or other visible characteristic which indicates a certain value or values at the location of that point analogous to a point on the skull. In order to generate discrete topographic display matrices having many thousands of display points from continuous analog waveforms at a limited, e.g. 20, number of points on the skull, the brain electrical activity mapping system, as illustrated in FIG. 2, converts the data to digital form and generates discrete sample frames 40, each sample or frame initially comprising 20 recorded values 41 from 20 channels of information. The system treats related groups of samples 40 as segments 42. In the case of EP data, for example, a segment would consist of a series of frames or samples, each 4 milliseconds in length, the series together representing one transient response sequence from the beginning of a pre-stimulus period to the end of the post-stimulus transient response. In the case of steady-state EEG data, a segment would consist of 2 seconds of data divided into 256 samples. A spectral analysis of the EEG data then produces 256 samples, each of which reflects the energy level in a small, e.g. ½ Hz, energy band and a segment consists of the entire series of 256 spectral samples. For signal averaging purposes, the system considers a set of segments together, e.g., 500 segments each representing a transient response to a given stimulus. The 500 segments taken together are known as an ensemble 43. Frames of data can be raw data or data which has been processed or transformed by the system. In any case, as illustrated in FIG. 3, when a frame 40 is to be displayed it is expanded into a matrix 45 consisting of a large number of display points 46 which are determined by an interpolation process from the original frame data points 47. Each point of the matrix is then converted to a visual display point 47 which forms part of the final topographic display 48.

Figure 4:
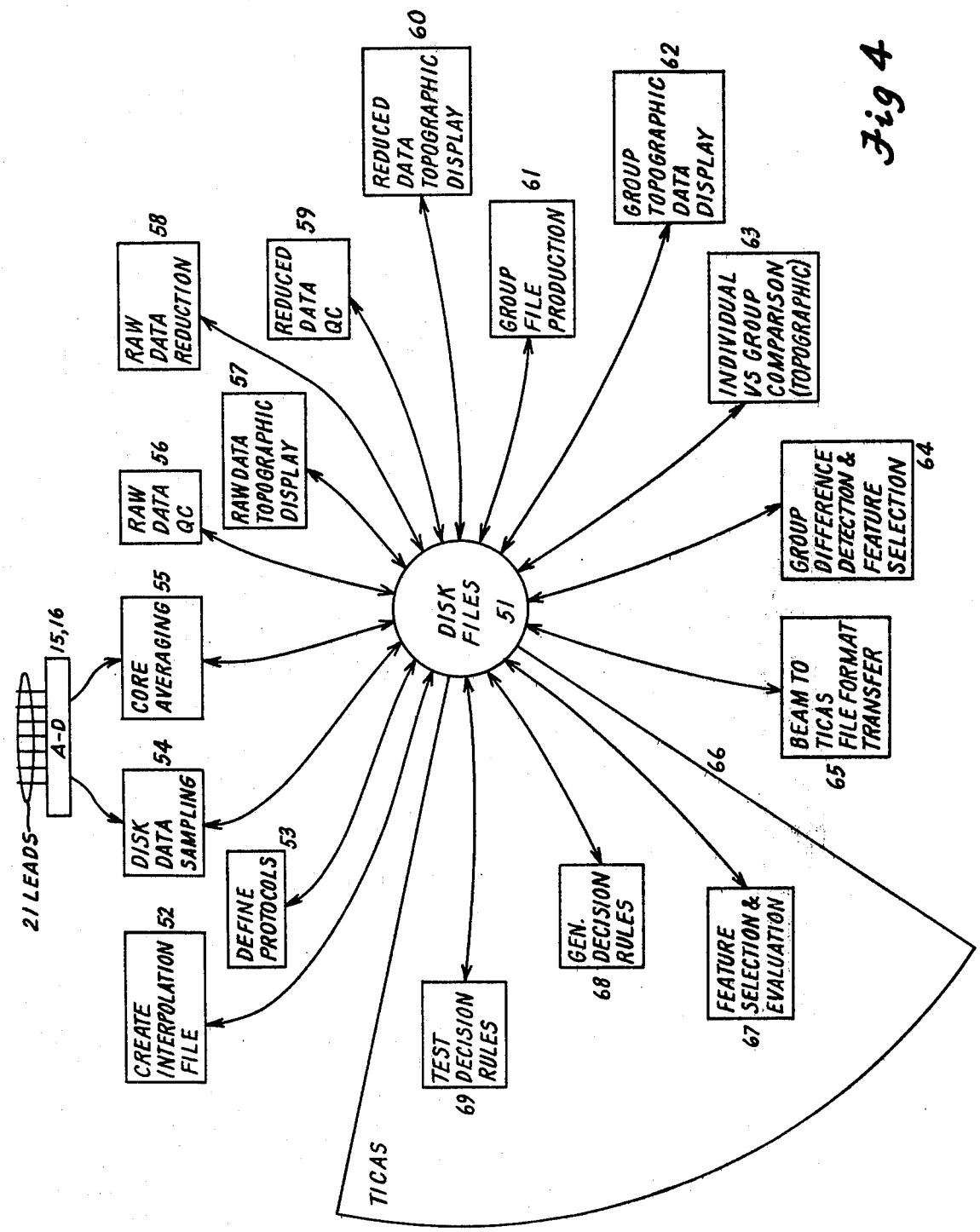
FIG. 4 is a block diagram of the functions performed by the BEAM system.

FIG. 4 illustrates the organization of the operations which comprise brain electrical activity mapping software 28 and TICAS analytic software 29. Raw and processed data is stored in disk files 51. Operations 52–65 and 67–69 use data stored in files 51 to perform data manipulation, data display and data storage functions. Operations 54 and 55 also process data from the outputs of converters 15, 16.

Figure 5:
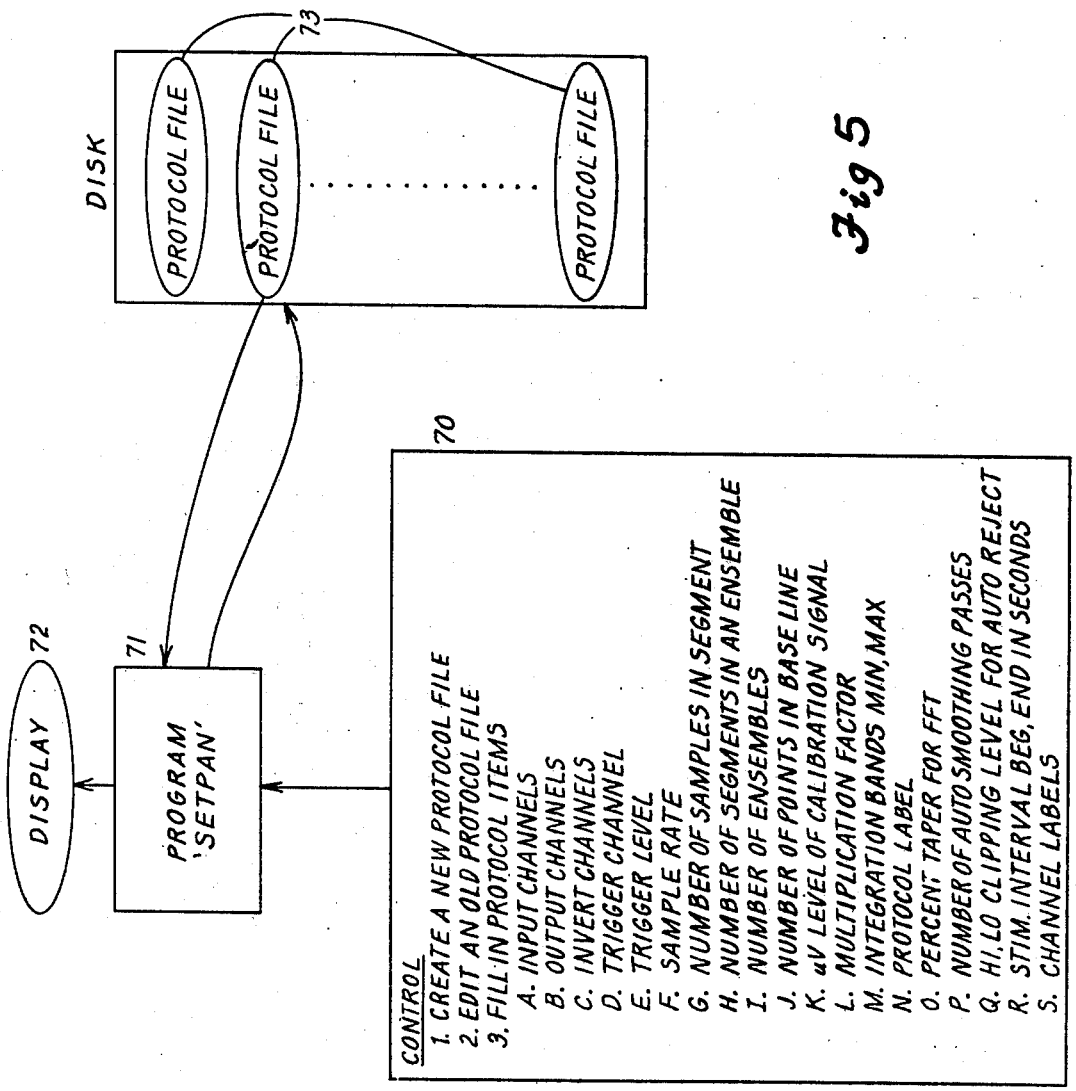
FIG. 5 is block diagram of the define protocols operation.

FIG. 5 illustrates the function of define protocols operation 53. Protocol files 73 are generated and edited by program 'SETPAR' 71 based on control information 70 provided by the operator through terminal 22, the results of the operation being displayed (block 72) on terminal 22 to the operator. Each protocol file 73 contains information which governs the manner in which other operations are performed on a particular type of data file (e.g., one protocol might apply to the processing of EP transient response data from strobe light stimuli). The protocol information may include the number and identity of input channels, the labeling of the output channels to correspond to specific points on the final display, the identity of the trial marker channel, the voltage level above which to search for the trial markers, the rate in samples per second of sampling of the data, the number of samples in a segment, the number of segments in an ensemble, the number of ensembles, the number of points in a baseline, the microvolt level of the calibration signal (e.g., 100 microvolts at 10 Hz), a multiplication factor, the number (up to 20) and size (width) of integration bands, the label of the protocol, the percent of taper of samples in a segment of data for fast fourier transform processing, the number of automatic smoothing passes, the high and low values for automatic rejection of data during accumulation, the stimulus interval and location in seconds, and channel labels related to electrode positions on the skull.

Figure 6:
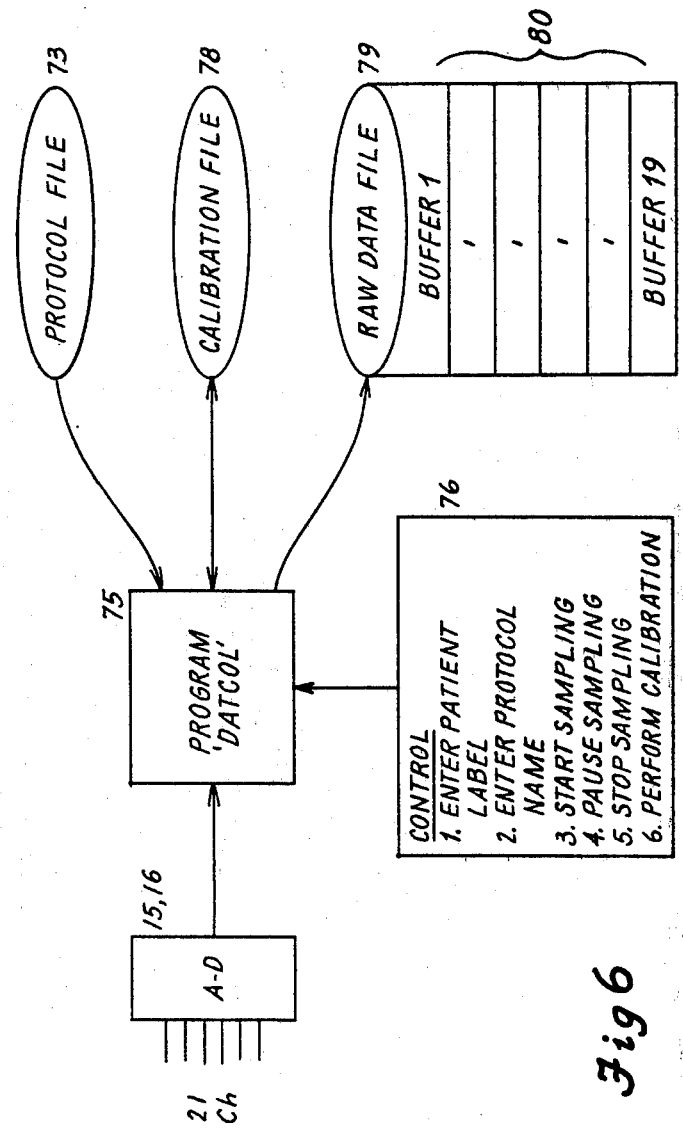
FIG. 6 is a block diagram of the disk data sampling operation.

FIG. 6 illustrates the function of disk data sampling operation 54. Program 'DATCOL' 75 loads raw data from the output of converters 15, 16 into raw data file 79, which is divided into 19 buffers 80 which hold ensembles of data related to particular brain states or stimuli. The operator provides control information 76 designating the patient to whom the data relates and the name of the applicable protocol file 73. Other control information 76 governs the beginning, end, and pauses in data sampling, and the performance of a calibration of signal levels. Calibration data is initially stored in a buffer 80 of raw data file 79. When the operator requests (block 76) a calibration, and designates which buffer 80 contains the raw calibration data, program 'DATCOL' computes the root mean square value and the mean of at least 30,000 points in each channel of calibration data and divides the root mean square value by 0.707 to establish the assumed peak value of the calibration signal. The peak value, representing the level of the original calibration voltage, and the mean value, representing the D.C. offset of the calibration voltage value for each channel, are stored in calibration file 78.

Figure 7:
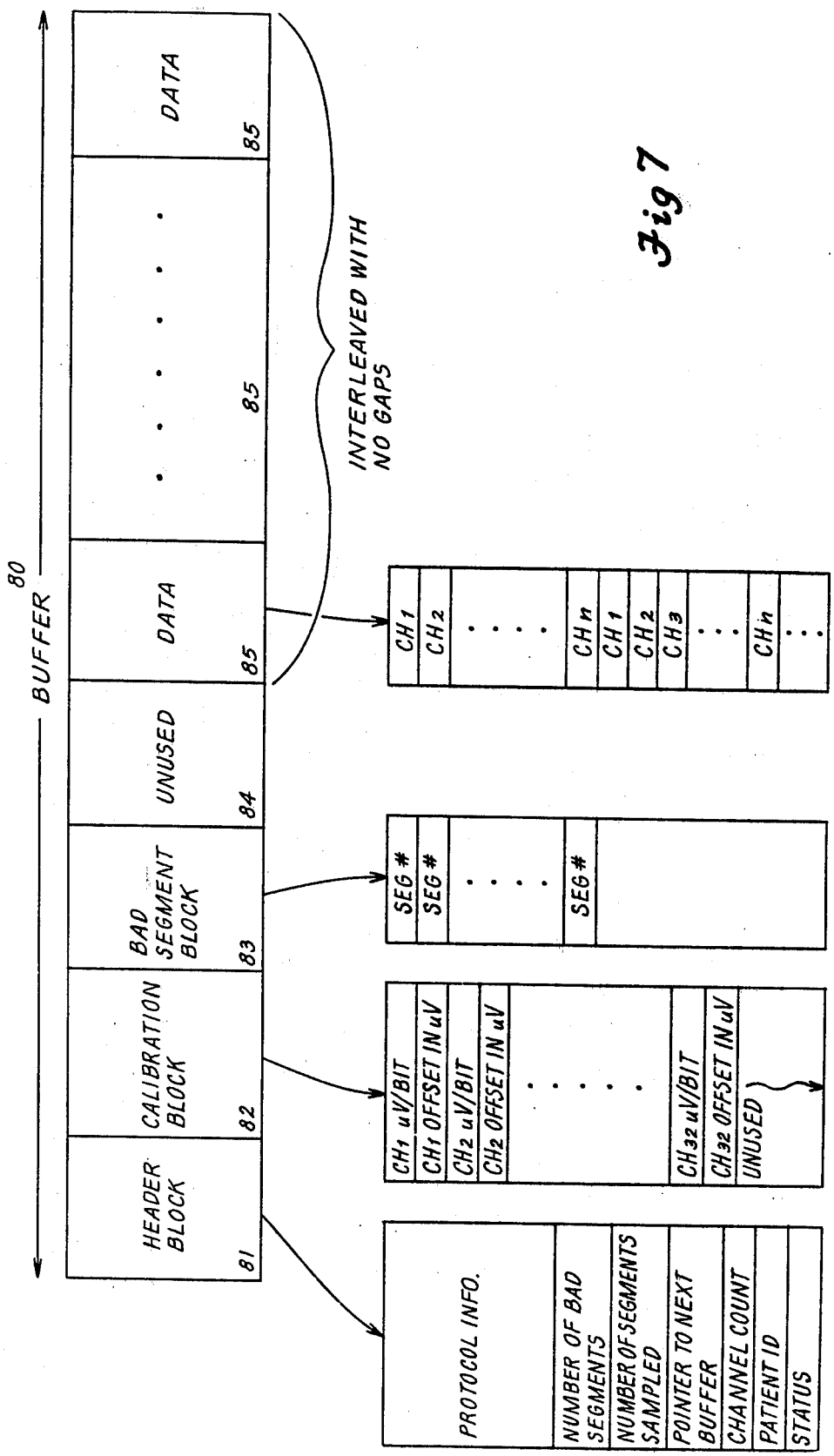
FIG. 7 is a data file format diagram of the raw data file.

The format of raw data as stored in raw data file 79 is illustrated in FIG. 7. Each buffer 80 contains header block 81, having protocol and other housekeeping information concerning the data stored in the buffer; calibration block 82 containing for each channel of data the calibration value in microvolts per bit and the number of microvolts by which the calibration signal was offset from zero both of which values were found in calibration file 78 at the time raw data was loaded; bad segment block 83 identifying segments of data which the operator will later decide to exclude from subsequent operations; an unused segment 84; and a series of data segments 85, which hold a series of data samples, each containing values for all 20 channels. The data segments 85 are interleaved with no gaps.

Figure 8:
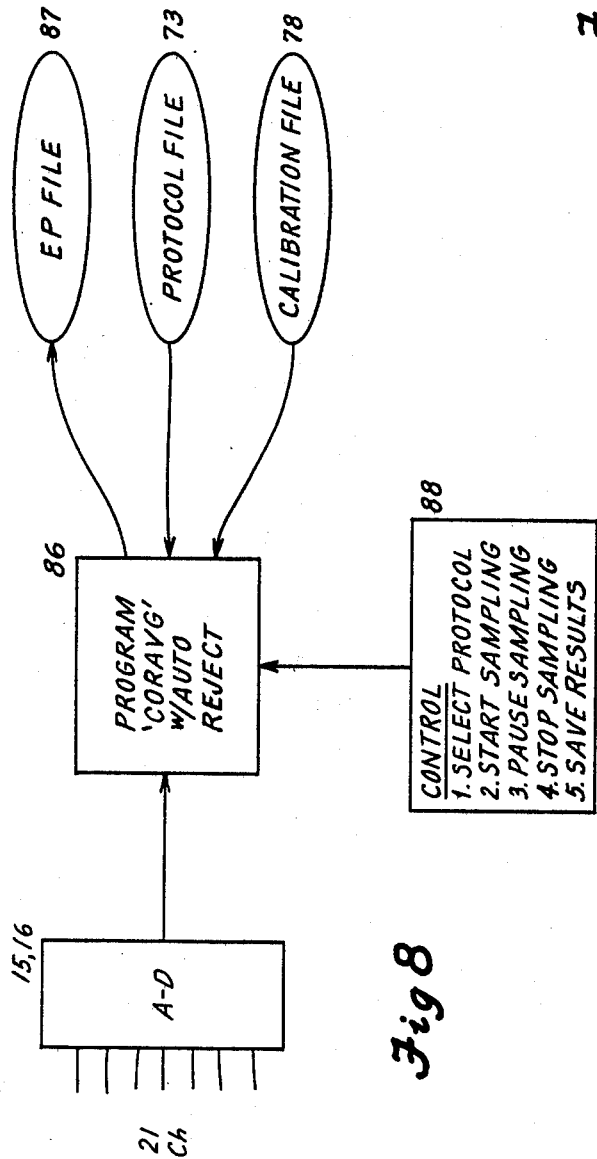
FIG. 8 is a block diagram of the core averaging operation.

FIG. 8 illustrates the function of core averaging operation 55, usually usef for loading and signal averaging raw EP transient responses. Data from converters 15, 16 is read by program 'CORAVG' 86. User provided control information 88 designates the protocol, obtained from protcol file 73, under which the operation is performed, and determines start, end, and pauses of the operation. Program 'CORAVG' 86 samples data beginning at points labeled by the prerecorded trial markers and forms signal averaged EP transient responses from a series of transient responses resulting from repetition of a stimulus. The series of transient response data are accumulated and held in EP file 87, which is a reduced data file as described below. Calibration file 78 holds calibration information accumulated from the data channels in the manner previously described. Program 'CORAVG' 86 automatically rejects as "bad data" any segment which contains values outside of preset limits. Program 'CORAVG' also automatically adjusts the zero baseline with respect to each electrode's average EP transiet response, by subtracting the mean of the pre-stimulus period values for a channel from each point in that channel's transient response curve.

Figure 9:
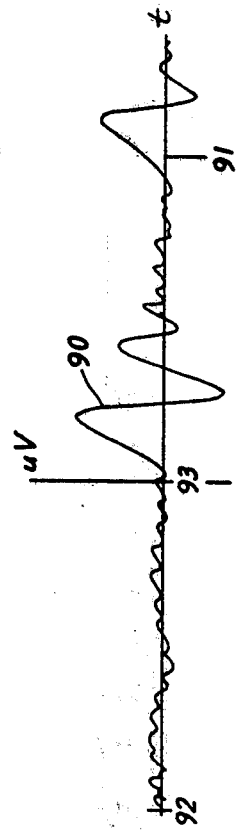
FIG. 9 is a graph of an average EP transient response waveform after automatic baseline zeroing.

FIG. 9 illustrates a plot of an average EP transient response 90 of microvoltage against time as it could be displayed on monitor 18 following core averaging operation 55. The stimulus was presented at time 93, the transient response includes pre-stimulus period between time 92 and time 93, and the plot shows calculated zero baseline 91.

Figure 10:
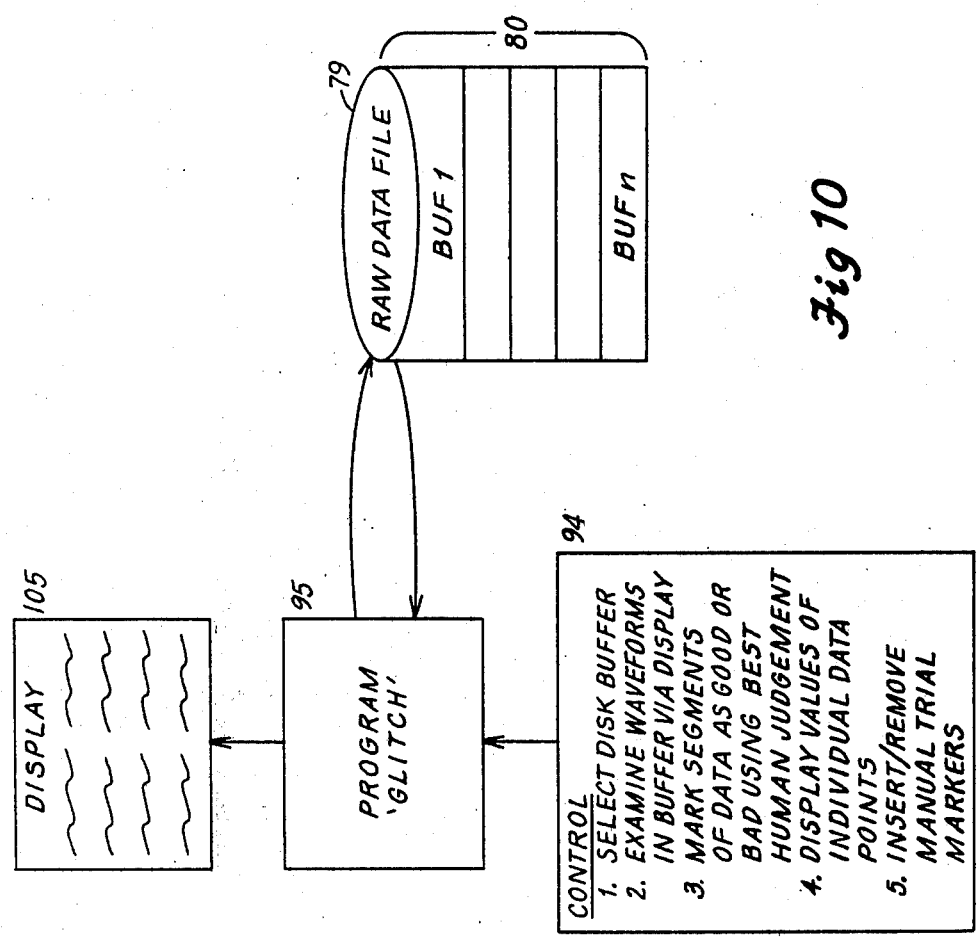
FIG. 10 is a block diagram of the raw data quality control operation.

FIG. 10 illustrates the function of raw data quality control operation 56, which enables the operator interactively to review and eliminate bad segments of raw data before other operations are performed. By means of control information 94 the operator can select for review the contents of any buffer 80 in raw data file 79. The buffer data is displayed (block 105) segment by segment by program 'GLITCH' 95 on television monitor 18 to the operator as an analog waveform. The operator can label any segment of bad data, which causes the bad data segment to be identified on bad segment block 83. Control information 94 can also include the insertion of trial markers indicating a point on a waveform at which subsequent operations should begin, and display to the operator the microvolt value of individual points on a displayed curve.

Figure 11:
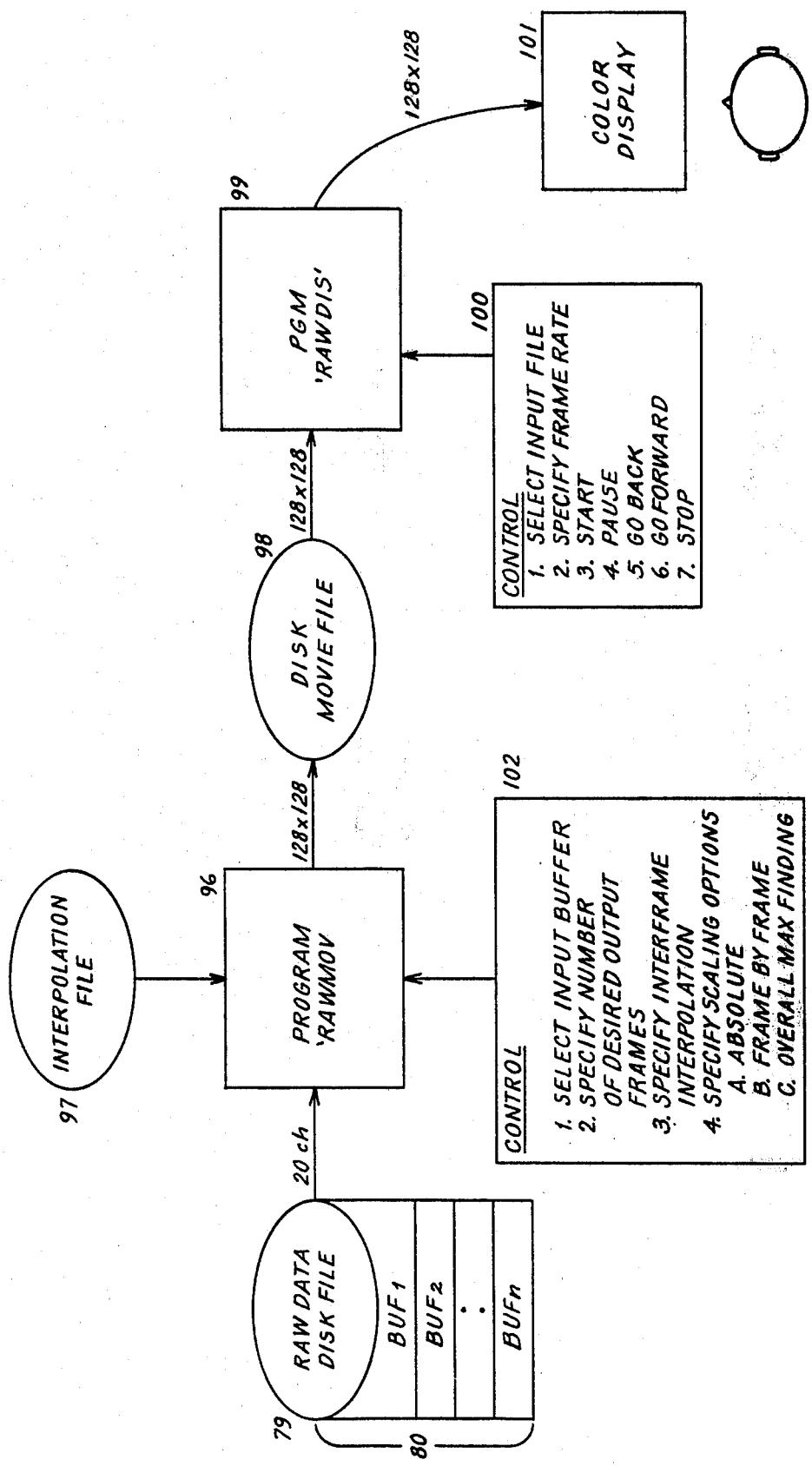
FIG. 11 is a block diagram of the raw data topographic display operation.

FIG. 11 illustrates raw data topographic display operation 57, which provides topographic time sequenced displays (cartoons) of raw data frames. Program 'RAWMOV' 96 expands the 20 channels of each data frame into a matrix of 128×128 data points by three-point linear interpolation. The operator provides control information 102 designating the disk buffer 80 on raw data file 79 which contains the data to be displayed; the number of display matrices to be produced; the parameters for interframe interpolation; and the parameters and options (described below) for scaling the data points among the available grey color tones of the display. Program 'RAWMOV' 96 calculates each interpolated data point for the display matrix using three-point linear interpolation from the three closest original channels and scales the data to the available grey color tones of the display. The interpolation is performed using preset coefficients stored in interpolation file 97 by an operation described below.

The display matrices produced by program 'RAWMOV' 96 are stored in sequence in disk movie file 98. Program 'RAWDIS' will display (block 101) the frames stored in disk movie file 98 on monitor 20. Control information 100 permits the operator to designate the file to be displayed, the frame rate, and the starting, stopping and reversing of the display sequence. The displays include labels of information taken from the protocol block, e.g., patient identification.

Figure 12:
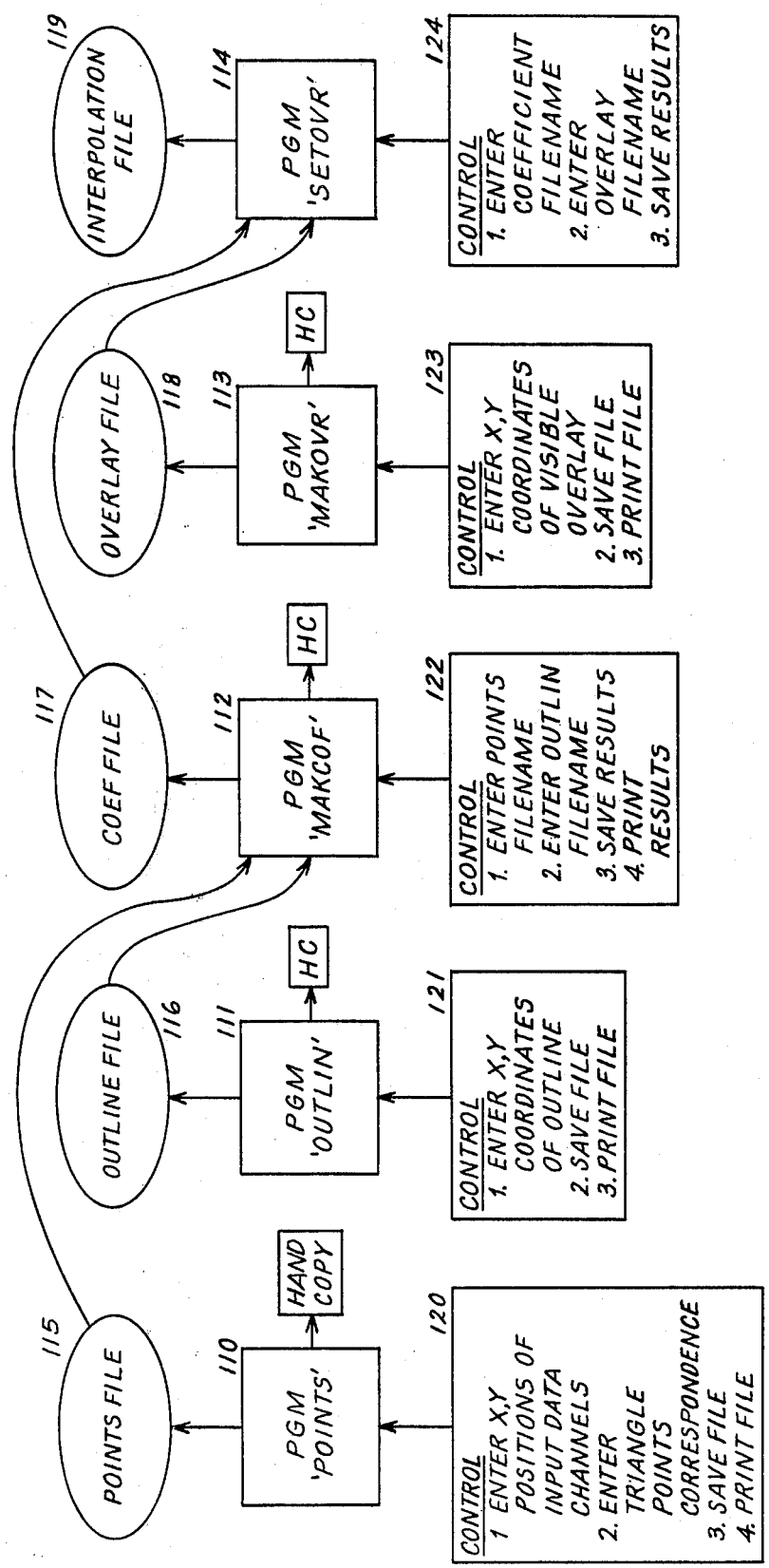
FIG. 12 is a block diagram of the create interpolation file operation.

FIG. 12 illustrates the functions of create interpolation file operation 52. Program 'POINTS' 110 creates points file 115 reflecting the X and Y coordinates of each point in the original electrode layout with respect to the 128×128 grid and associating with each point in the 128×128 display matrix the identity of the three original electrode points with respect to which it should be interpolated. Control information 120 provided by the operator includes the X and Y coordinates of each channel and the identity of the three interpolation points for each display point. Program 'OUTLINE' 111 identifies and stores in outline file 116 the X and Y coordinates of the points which outline the plan view of the skull to be included in the display, based on control information 121. Program 'MAKCOF' 112 generates and stores in coefficient file 117 the coefficients needed to perform the three-point linear interpolation for each matrix display point within the skull outline, using points file 115 and outline file 116 as input. Program 'MAKOVR' 113 stores in overlay file 118 the operator provided (block 123) coordinates of the overlay of the skull, nose and ears outline for the display. Program 'SETOVR' 114 generates interpolation file 119 from overlay file 118 and coefficient file 117. Interpolation file 119 then contains the information required to compute interpolated matrix data points and the skull overlay for display.

Figure 13:
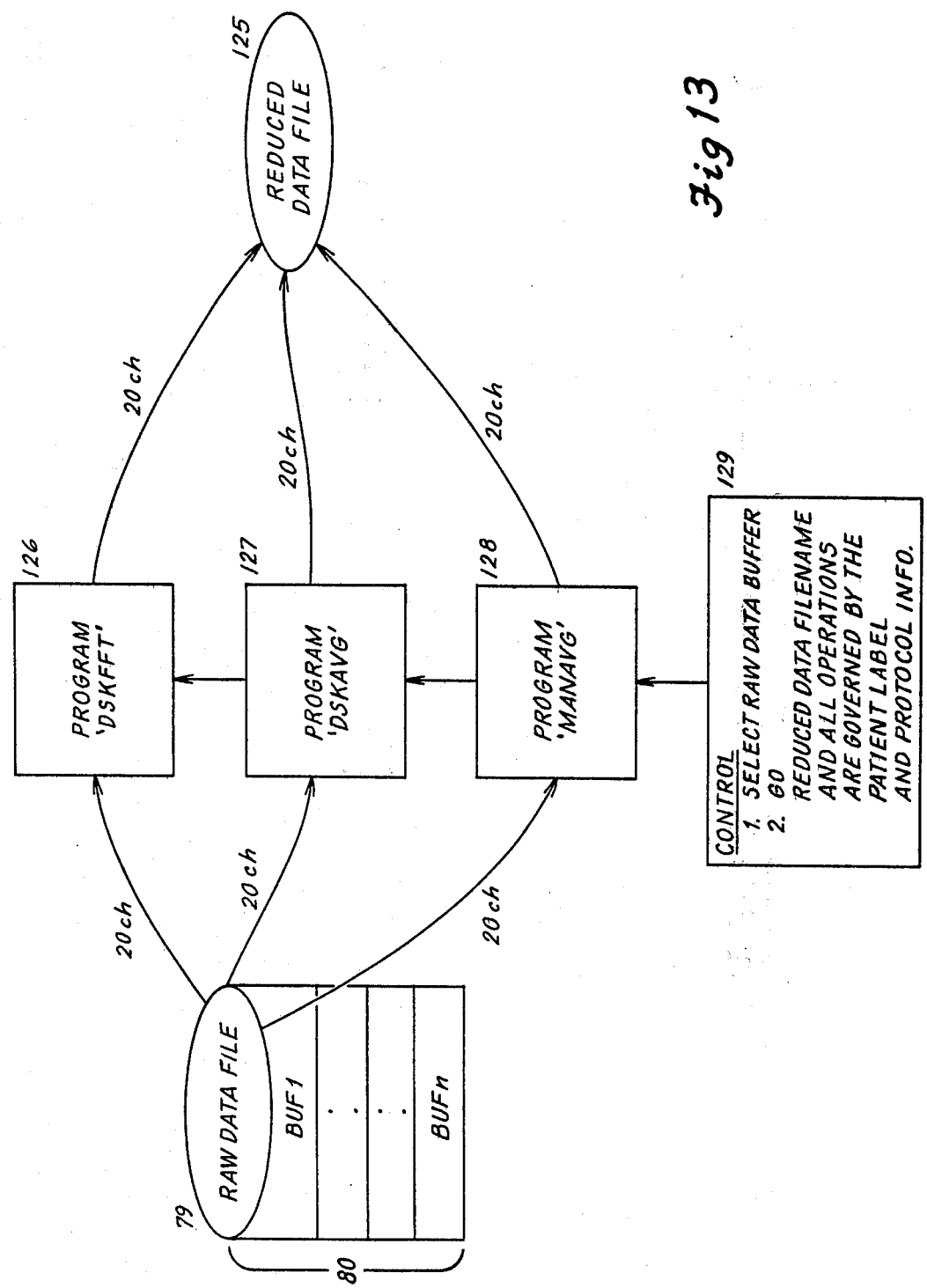
FIG. 13 is a block diagram of the raw data reduction operation.

FIG. 13 illustrates the function of the raw data reduction operation 58. Three alternative programs can operate on data in buffers 80 to produce reduced data files 125. Program 'DSKFFT' 126 accepts segments of EEG data from raw data file 79, performs a fast fourier transform analysis which produces a new segment of data reflecting the spectral energy in each of a sequence of frequency bands. Program 'DSKFFT' 126 also generates, for each group of segments, an ensemble consisting of the sums (used in a later step to form the average values) and sums squared (used in a later step to form the standard deviations) for each channel across all segments in the group, values reflecting each of the sums as a percentage of the total spectral energy in the segment, and values reflecting the coefficient of variation (the standard deviation divided by the mean) for each channel across an ensemble. FIG. 15 illustrates the format of the resulting ensemble of FFT data stored in reduced data file 125. The sums data 130 is filed in sequence by channel for the first frequency band 131, e.g., 0.5 Hz. Similar sums data follows for the other frequency bands. After all sums data is stored, the sums squared data 132, the normalized power spectral density sums, and the coefficient of variation data are stored in similar fashion. In addition to storing the sums and sums squared data for all segments in the ensemble, program 'DSKFFT' can store spectral information for each segment analyzed. As illustrated in FIG. 16, the data is stored as sine and cosine coefficients for each channel for each frequency band, and as normalized sine and cosine coefficients as a percentage of total spectral energy. As illustrated in FIG. 18, the FFt data file 191 stored on reduced data file 125 also includes a header block 192 housekeeping information.

In FIG. 13, program 'DSKAVG' 127 performs a function similar to core averaging operation 55 in signal averaging EP transient response waveforms, but uses as input raw data stored in raw data file 79 and permits the operator to review each waveform and select those to be used in the averaging process, rejecting others. Program 'MANAVG' 128 permits a similar operator-assisted signal averaging process when the raw data does no contain preset stimulus trial markers, requiring the operator to indicate the point at which averaging is to begin for each waveform. FIG. 14 illustrates the format of signal averaged data produced by programs 'CORAVG' 86, 'DSKAVG' 127 and 'MANAVG' 128. The sums of each channel for all trials for the first time frame 133, e.g., 0-4 milliseconds, are loaded in order, followed by similar information with respect to all subsequent time frames for a given segment. As illustrated in FIG. 17, such EP files 190 are preceded by header block 193.

Figure 19:
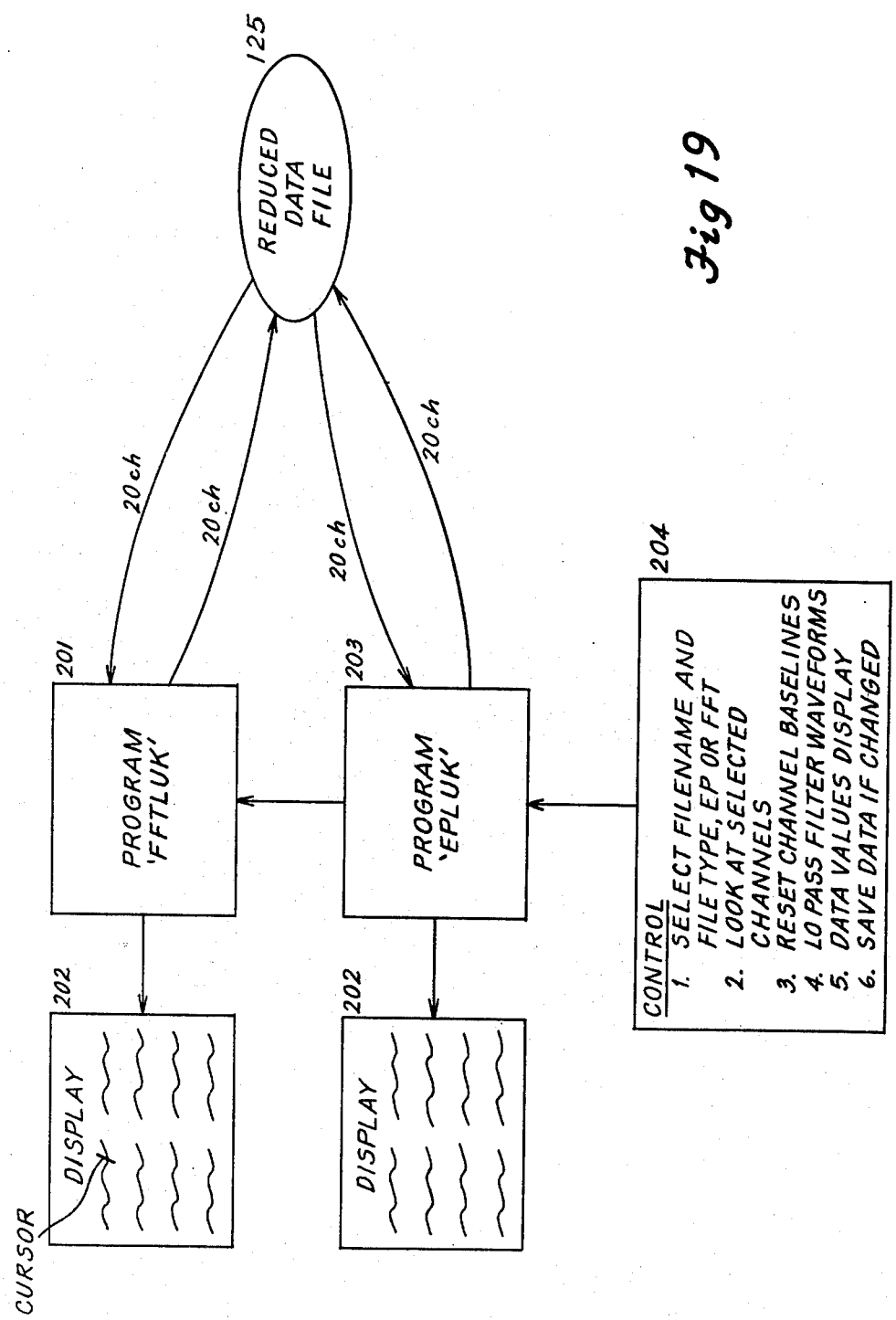
FIG. 19 is a block diagram of the reduced data quality control operation.
Figure 20:
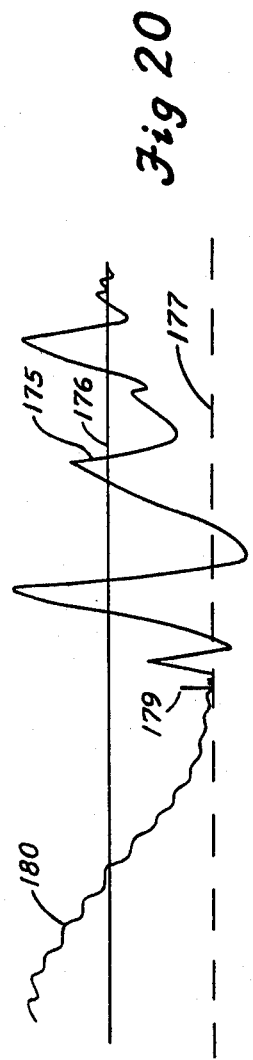
FIG. 20 is a graph of an average EP transient response waveform after automatic baseline zeroing and after manual baseline readjustment.

FIG. 19 illustrates the function of reduced data quality control operation 59, which permits the operator interactively to review and modify data in reduced data file 125. By providing control information 204, the operator can select the file to be reviewed and indicate whether it contains FFT spectral information or EP time-sequenced information. For FFT information, program 'FFTLUK' 201 displays (block 202) selected channels of spectral data as frequency-voltage curves on monitor 18 and permits the operator to low-pass filter the waveforms and display the value of particular data points. For EP data, program 'EPLUK' 203 displays (block 202) selected channels as time-voltage curves and permits the operator to reset the zero baseline, to filter high frequency noise from a channel, and to display the value of any point on a curve. FIG. 20 illustrates the function of manual baseline relocation. Because pre-stimulus period response 180 was not level, automatic baseline 176 set by program 'CORAVG' 86 inaccurately reflects the true zero level for transient response curve 175. The operator can relocate the baseline to a new level 177 by moving cursor 179 to the desired level, causing that voltage value to be subtracted from each point of data along curves 180 and 175.

Figure 21:
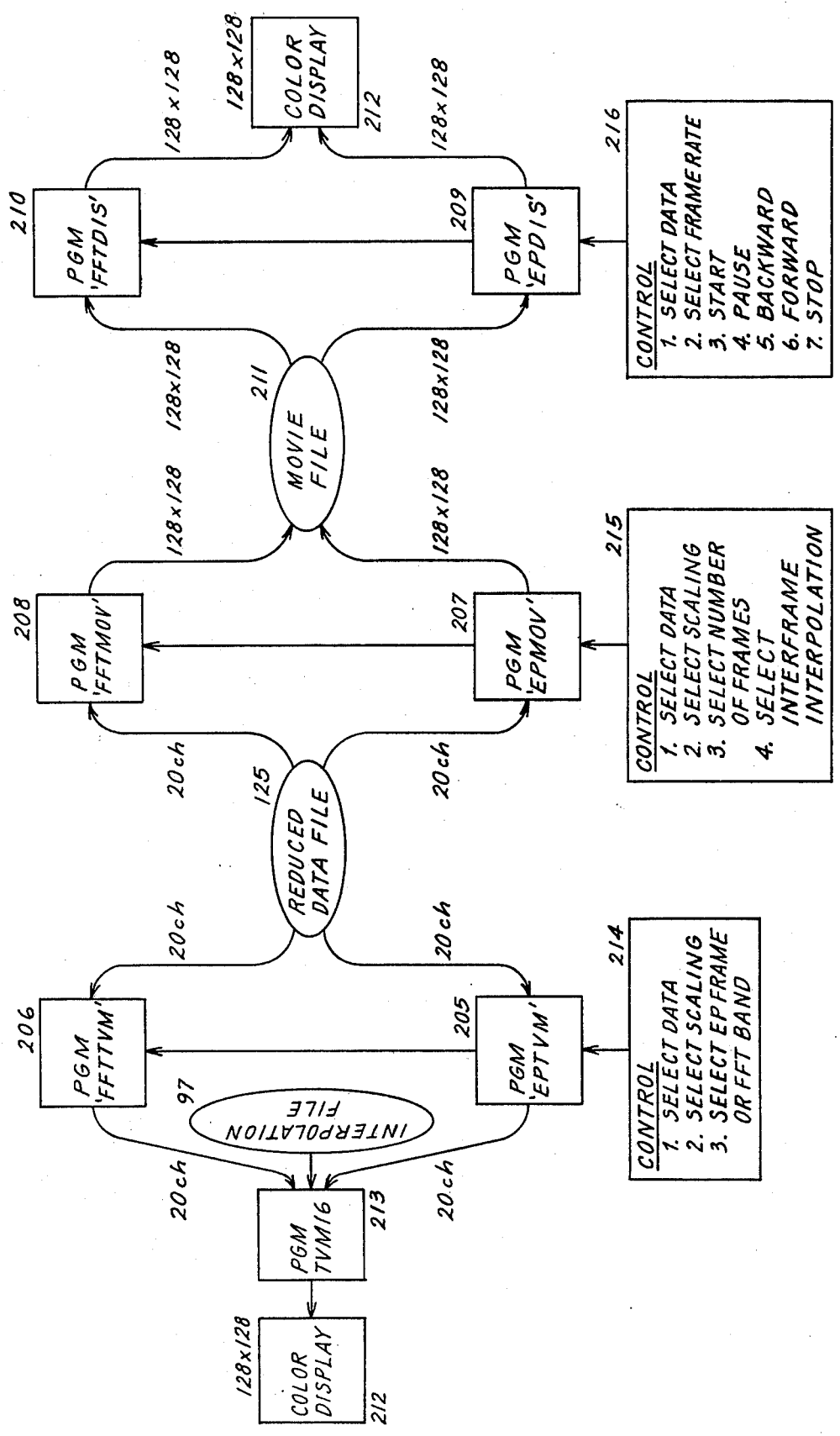
FIG. 21 is a block diagram of the reduced data topographic operation

FIG. 21 illustrates the functions of reduced data topographic display operation 60. For single frame display of FFt data, program 'FFTTVM' 206 reads data from reduced data file 125 as selected by operator control information 214. The data is scaled in accordance with instructions included in control information 214. The selected frame is provided to program 'TVM16' 213 which interpolates a matrix of 128×128 points using the coefficients and other information contained in interpolation file 97, and provides the resulting matrix to color display 212. For single frame EP display, program 'EPTVM' 205 performs an analogous process to that of program 'FFTTVM' 206. Programs 'EPTVM' 205 and 'FFTTVM' 206 also perform compilations of sequences of frames into one display matrix, in accordance with predefined groupings set forth in protocol blocks.

A sequence of FFT matrices or EP matrices can be displayed in rapid time sequence as a cartoon by the use of program 'FFTMOV' 208 and program 'EPMOV' 207, respectively, each of which processes sequences of selected matrices of data from reduced data file 125, using scaling control information 215; interpolates full 128>128 matrices for each frame; interpolates a selected number of additional matrices between the original frames; and stores the resulting matrices in movie file 211. Based on control information 216 specifying data to be displayed, the frame rate of display, start, stop, backward, forward and pause, program 'FFTDIS' 210 and program 'EPDIS' 209 provide cartooned matrices for viewing on color display 212.

Figure 22:
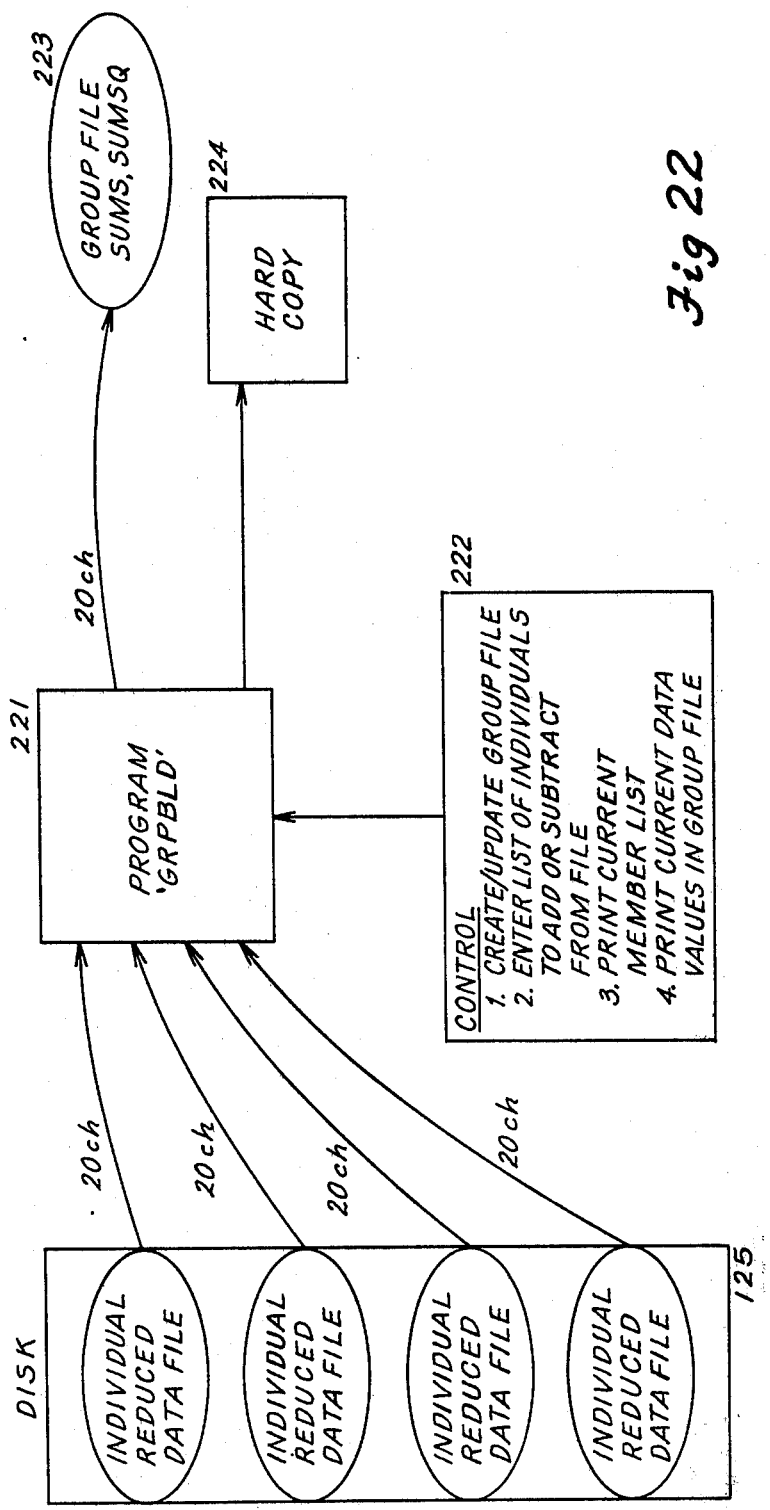
FIG. 22 is a block diagram of the group file production operation.

FIG. 22 illustrates group file production operation 61. Program 'GRPBLD' 221 creates and updates a composite group file 223 working from selected individual reduced data files 125. Control information 222 provided by the operator indicates the identity of individual reduced data files to be included. The group files 223 consist of the sums and the sums squared for all homologous points in the reduced data files 125 of all individuals in the group. Normalized sums and coefficients of variation may also be produced and stored. Hard copy 224 listing the individuals in each group and the values of group file data are available based on control information 222.

Figure 23:
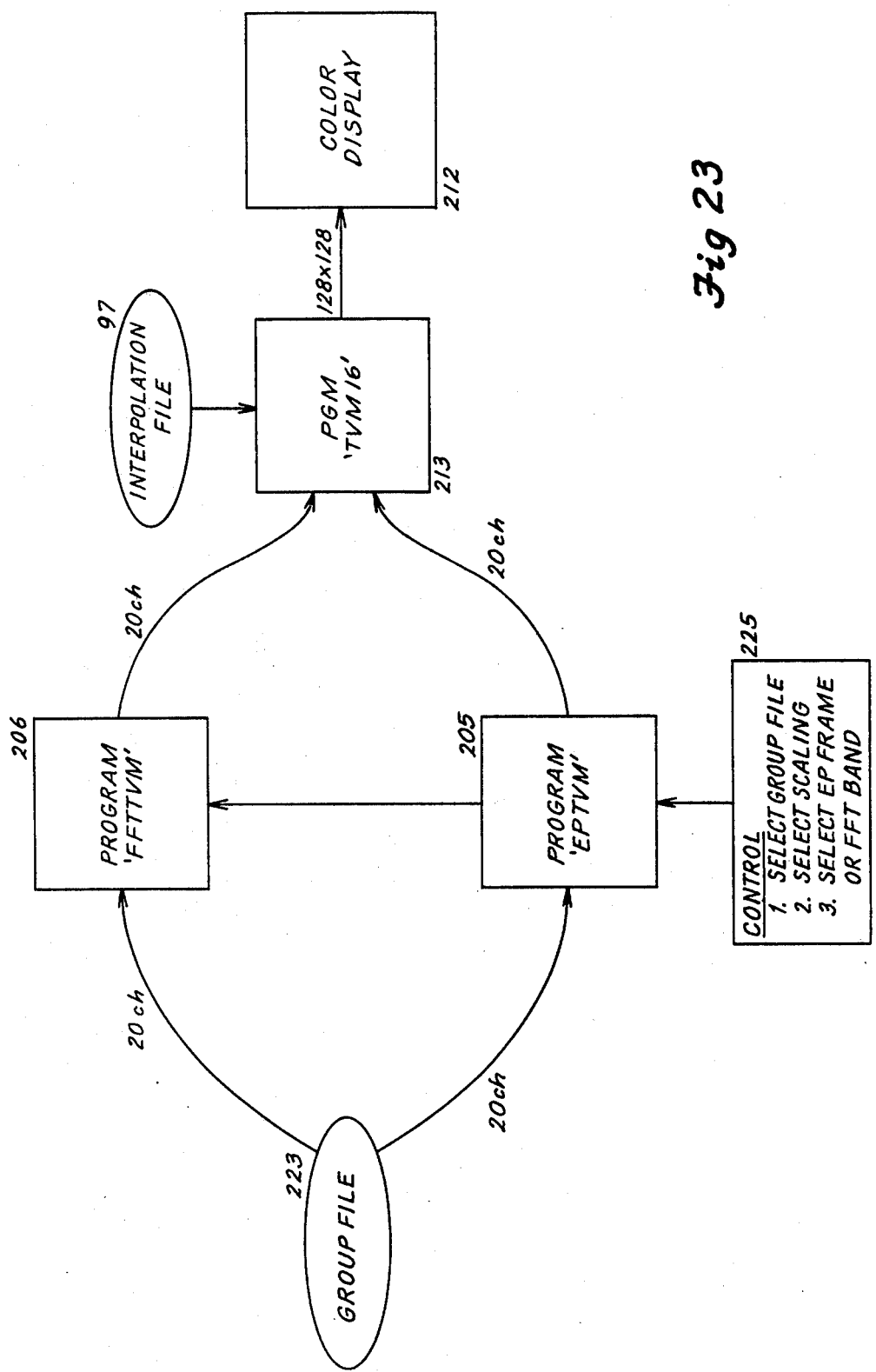
FIG. 23 is a block diagram of the group topographic display operation.

FIG. 23 illustrates the function of group topographic data display operation 62 which is analogous to the operation of the single frame display of reduced data file information, illustrated in FIG. 21, except that the data displayed is from group file 223 instead of reduced data file 125.

Figure 24:
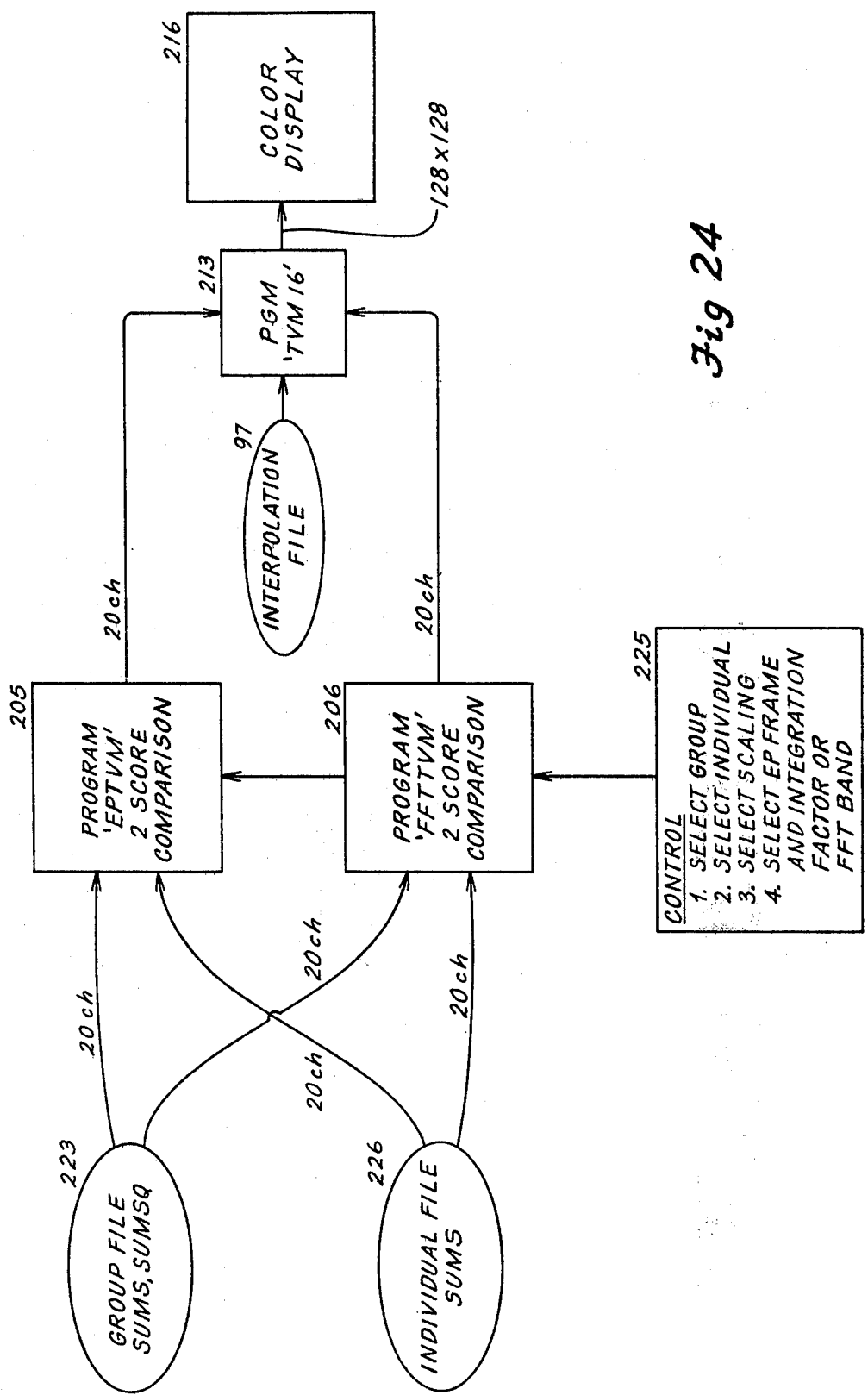
FIG. 24 is a block diagram of the individual vs. group comparison operation.

FIG. 24 illustrates the function of individual versus group comparison operation 63. Programs 'EPTVM' 205 and 'FFTTVM' 206 are performed respectively on EP and FTT data. In each case, the program generates a frame of points, each of which is the number of standard deviations (z-statistics) by which an individual's point, taken from individual file 226 differs from the average of the group's corresponding points taken from group file 223. The resulting frame is displayed (block 216) by program 'TVM16' 213, which interpolates additional data points to form a 128×128 matrix in the manner previously described.

Figure 25:
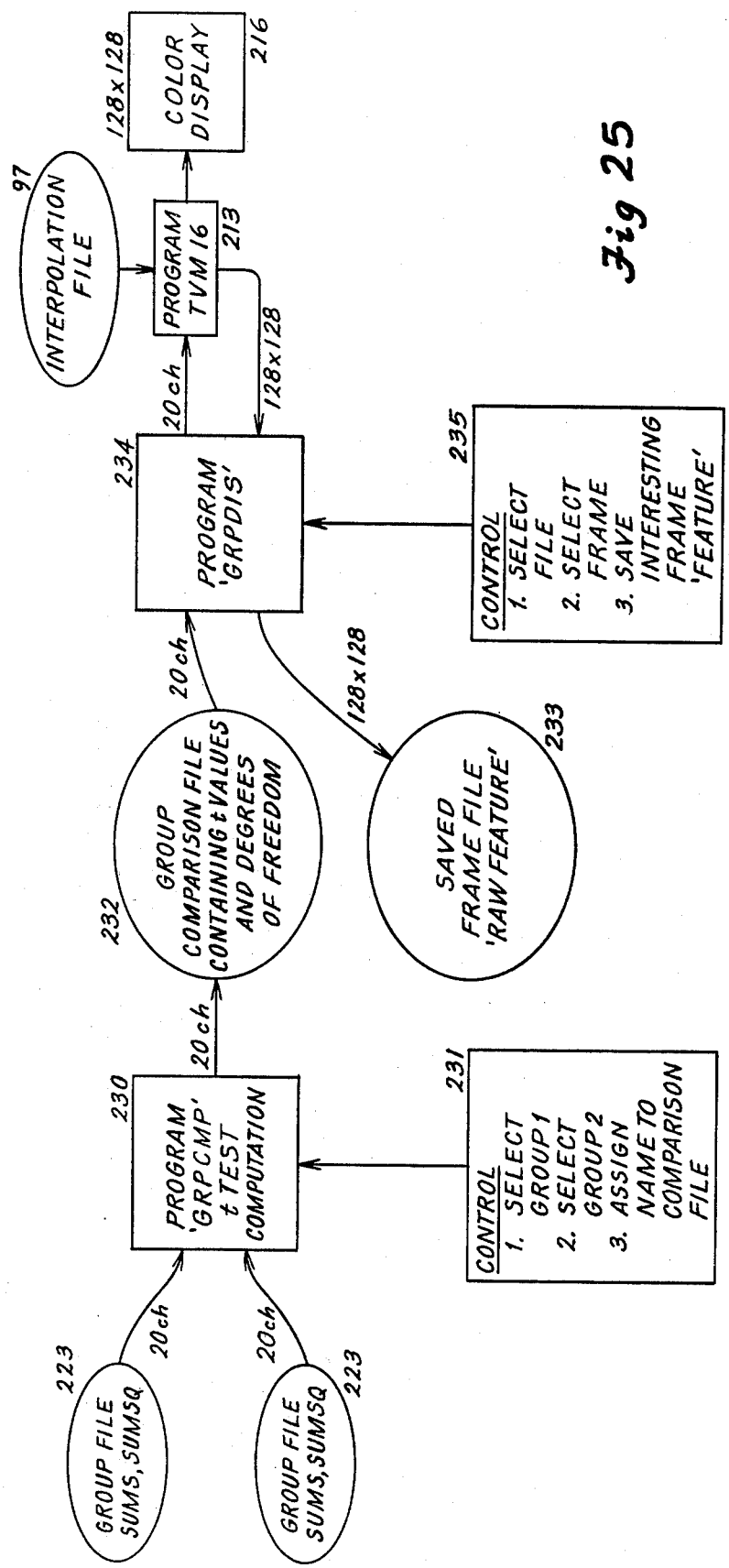
FIG. 25 is a block diagram of the group difference detection and feature selection operation.

FIG. 25 illustrates the function of group difference detection and feature selection operation 64, which computes frames of t-statistics reflecting the level of statistical difference between two groups based on the means and standard deviations of homologous data points for the two groups. Program 'GRPCMP' 230 computes t-statistics and degrees of freedom from the sums and sums squared data contained in two different group files 223 designated in control information 231 provided by the operator. The resulting frames are stored in group comparison file 232. Based on file and frame designations set forth by the operator in control information 235, program 'GRPDIS' 234 transmits a selected t-statistic frame for display by program 'TVM16' 213 as previously deascribed. Program 'TVM16' 213 also returns a fully expanded 128×128 matrix back to program 'GRPDIS' 234. Through control information 235, the operator may store such a t-statistic matrix in saved frame file 233. FIG. 26 illustrates the format of saved frame file 233. Header block 240 contains the number of saved frames, and for each frame identifies the time frame length or frequency band and the protocol under which the data was collected. Frames 241 contain 128×128 matrices of floating point t-statistics generated by program 'GRPDIS' 234.

Figure 27:
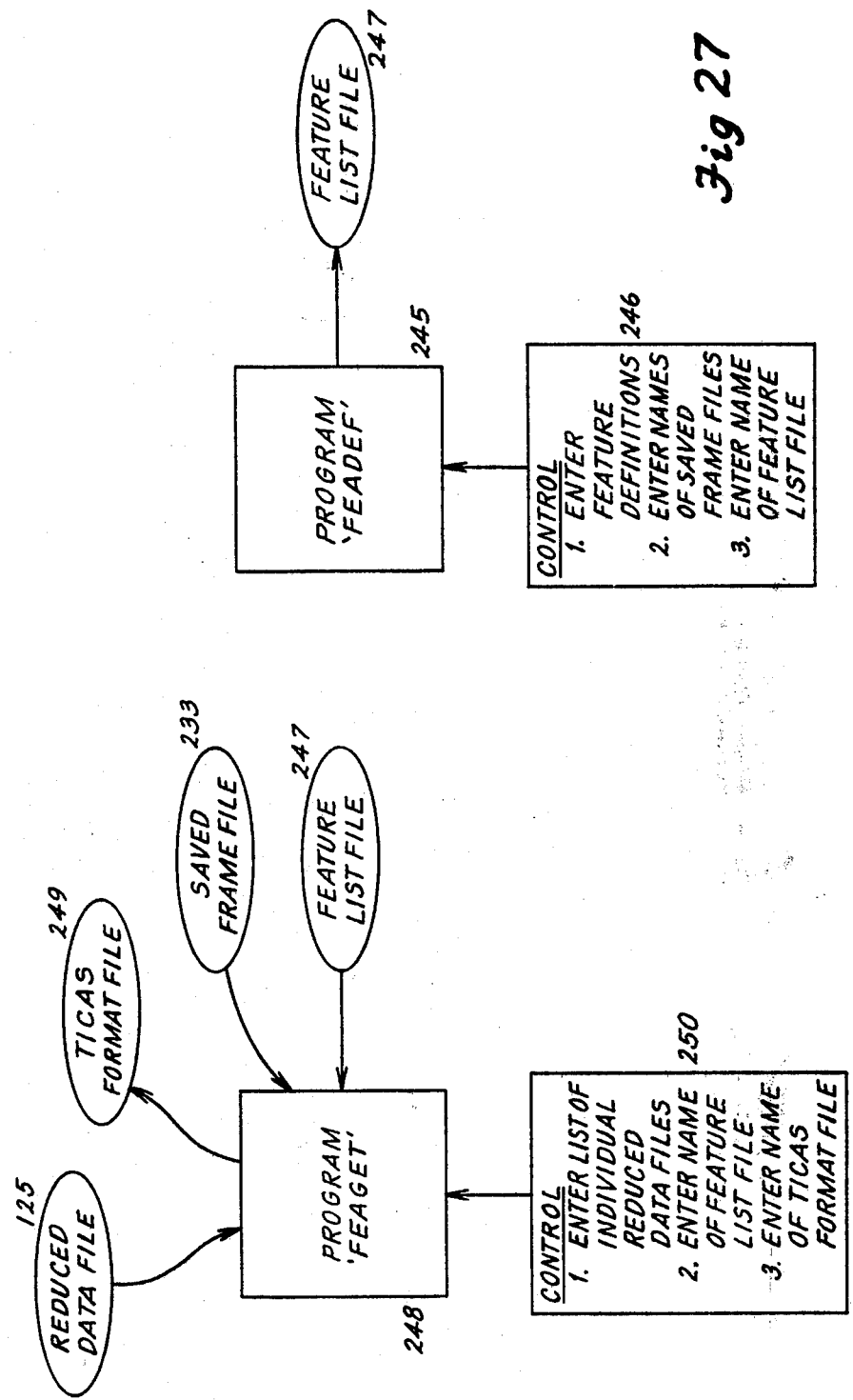
FIG. 27 is a block diagram of the brain electrical activity mapping to TICAS file transfer operation.

FIG. 27 illustrates the functions of the brain electrical activity mapping to TICAS file transfer operation 65, which converts features of brain electrical activity mapping data to a form usable with TICAS software 29. Program 'FEADEF' 245 generates feature list file 247 from feature definitions and names of saved frame files 234 provided by the operator in control information 246. Program 'FEAGET' 248 then generates TICAS formal file 249 from reduced data files 125, saved frame file 233, and feature list file 247, identified by the operator in control information 250. The feature definitions which may be selected and stored in TICAS format file 249 for subsequent TICAS analysis include nearly all combinations of data found in all individual files, all combinations of integrated bands of frames (e.g., alpha bands) in individual files grouped according to preset protocol specifications, or combinations of individual frame files weighted by the values in a saved t-statistic frame.

FIG. 28 illustrates the functions of TICAS feature selection and evaluation operation 67. In control information 266, 264 the operator designates two groups 262, 263 from TICAS format file 249 whose features are to be analyzed, the type of data to be analyzed, the number of input features to be analyzed, and the number of output features to be produced. Program 'UTEST' 261 peforms a standard two-sample Wilcox-Mann-Whitney U-test and provides a list of U-test scores in rank order which are printed on printer 23 and stored. Program 'FMTST' 260 performs a final merit value (FMV) test and provides and stores a list of values for features in order of final merit values. Program 'FMTST' 260 first determines intermediate merit values as a combination of the standard receiver operating characteristic (ROC) curve or d' value and the results of an ambiguity function analysis. The final merit values for each feature are then determined by correlation of the intermediate merit value with all features ranked higher in intermediate value. Program 'MERGE' 267 selects from Group A features 268 and group B features 269, based on the FMV values and U values, those features which are most useful, which are then stored in disk files 270 and 271.

Figure 29:
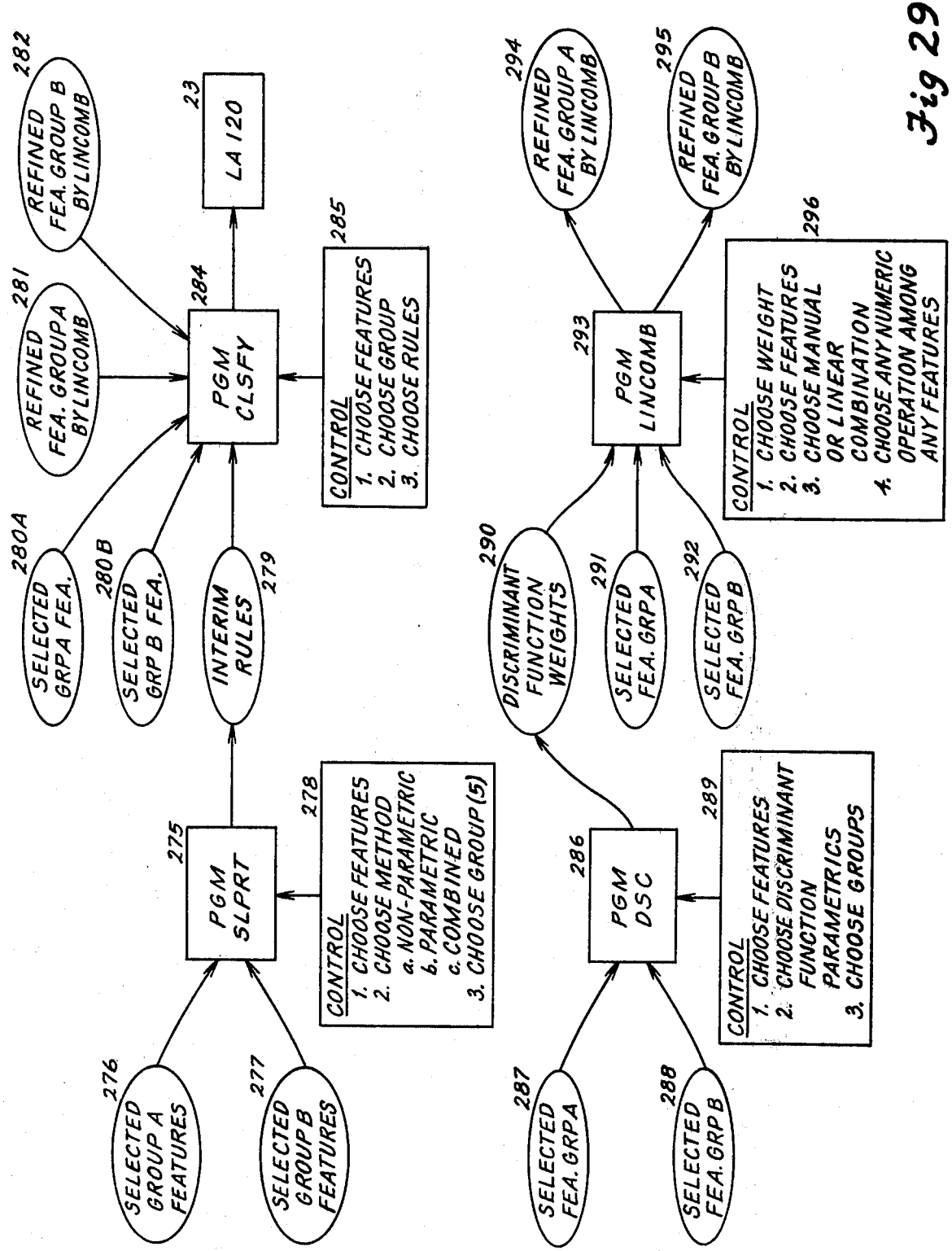
FIG. 29 is a block diagram of TICAS generate decision rules operation.

FIG. 29 illustrates the functions of TICAS generate discision rules operation 68. Program 'SLPRT' 275 uses an operator controlled (block 278) subset of selected Group A features 276 and selected Group B features 277 to generate disk stored interim rules 279, by a method controlled (block 278) by the operator. The computation method may be a non-parametric d-selection technique, a parametric classification technique, or a combination of the two. Program 'CLSFY' 284 uses operator selected (block 285) interim rules 279 to classify operator selected subjects having operator selected features, from selected group features files 280 or refined group features files 281, 282, printing the results on printer 23, thereby permitting the operator to evaluate the efficacy of each selected interim rule 279. Progran 'DSC' 286 combines operator chosen (289) features from selected Group A features 287 and selected Group B features 288 into new features on the basis of the weighting functions of a standard linear discriminate analysis, subject to the operator's choice (group 289) of discriminant function parameters. Discriminant function weights for the best features are then loaded into a disk file 290. Program 'LINCOM B' 293 uses the original selected Group A features 291 and selected Group B features 292 and the discriminate function weights 29 to create refined Group A features 294 and refined Group B features 295, which are linear or other operator selected (block 296) combinations of the original features. Refined Group A features 294 and refined Group B features 295 can replace the original selected features 276 and 277 as input to program 'SLPRT' 275 to permit an iterative process of decision rule generation.

Figure 30:
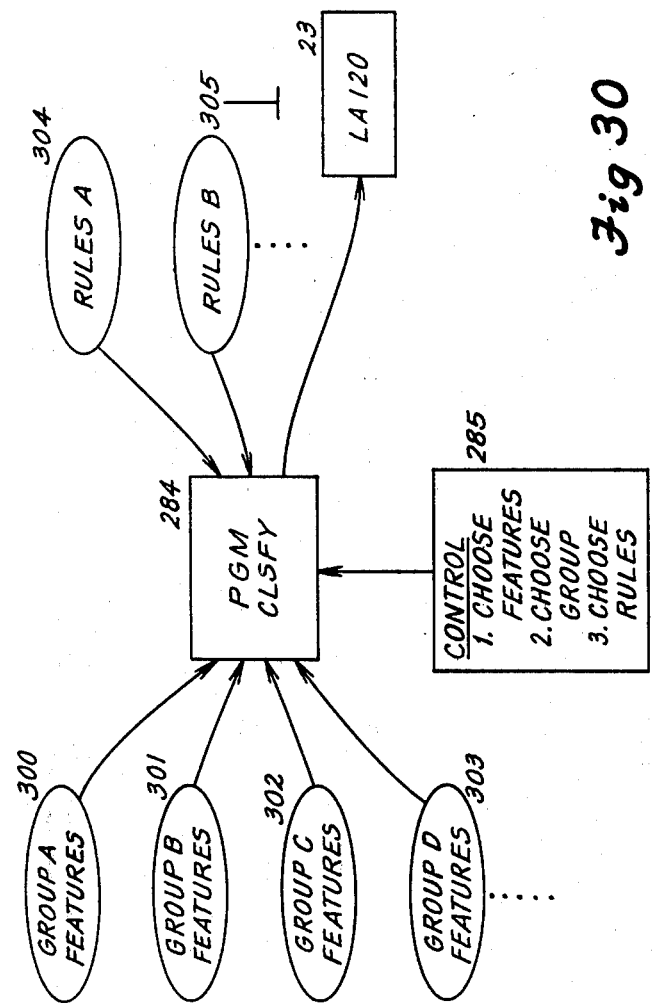
FIG. 30 is a block diagram of TICAs test decision rules operation.

FIG. 30 illustrates test decision rules operation 69. Program 'CLSFY' 284 uses final sets of decision rules, e.g., rules A 304 and rules B 305, to classify individuals in original Group A 300, original Group B 301 and new unknown groups, e.g., Group C 302 and Group D 303, to determine the efficacy of the final decision rules, the results being provided on printer 23.

Operation

Data Gathering

Accumulation of raw EEG and EP data is accomplished by first attaching 20 electrodes 5 to the scalp of an individual subject in a conventional international 10-20 format. In other embodiments, information from between 10 and 200 electrodes can be gathered and analyzed. Before recording, and if desired during recording, the operator observes the signal levels on the 20 channels of chart recording of polygraph 10 and adjusts the gain on weak signals to produce usable waveforms. A calibration signal of 100 microvolts (10 Hz) from source 8 is recorded on all twenty channels on tape recorder 11 at the beginning of each session and whenever any of the gain levels on polygraph 10 is adjusted.

Data gathering typically begins with a careful administration of a sequence of tests, each of which is intended to establish a particular steady-state electrical condition in the subject's brain. The sequence of tests usually includes instructions to relax and remain still with eyes open, to relax and remain still with eyes closed, to become drowsy, to breathe deeply for hyperventilation, to listen to music and to listen to speech. Other tests rewquire the subject to (1) listen carefully to a story and answer simple questions about its content when completed, (2) remember a set of six abstract figures (often resembling an unknown language alphabet) in black ink on index cards presented by the examiner, (Kimura Figures-Instruction) (3) select the six previously presented figures from a set of 38 figures, verbally indicating yes or no (Kimura Figures-Test), (4) associate each of four abstract figures on index cards with a particular artificial name spoken by the examiner (Paired Associates-Instruction), (5) name each of the four abstract figures when tested by the examiner (Paired Associates-Test), (6) read silently three previously unread paragraphs (e.g., example text from the Gray Oral Reading Test) so as to answer questions subsequently (Reading Test-Instruction), (7) identify whether 34 typed sentences presented by the examiner were previously included in the three paragraphs (Reading Test-Test), and (8) read text upside down: The tests are designed to permit recording of brain electrical signals during simple resting brain activity and during different levels of activation of the left hemisphere, the right hemisphere and both hemispheres of the brain together. This permits the demonstration of pathologies present at rest and those present upon brain activation. The development of specific tests and the choice of tests is determined by the user based in part on the subject being tested and the information eing sought as described in greater detail below. Between twenty seconds and three minutes of steady state brain electrical activity is recorded on all 20 channels during each of the tests. Appropriate records of the tape location of each test are kept. These tests have been used with the brain electrical activity mapping system to demonstrate group differences between normal subjects and those with dyslexia or specific reading disability at the 10-12 year age level and at the six-year age level; to differentiatedemented patients from normals and aged patients from younger patients in clinical settings; to identify patients with an organic basis for sociopathic behavior and other forms of mental illness; to demonstrate epilepsy when the resting background EEG failed to show any abnormalities; to demonstrate abnormalities in EEg and EP data for schizophrenic subjects; and to determine when a brain tumor, previously treated, is about to recur.

With young infants, the brain states tested include sleep, alert and attending to visual and auditory stimuli, alert but not attending to visual and auditory information, and drowsiness. Using these states, it is possible to discriminate among children with poor behavioral scores on a psychological test and those with high psychological scores.

A series of sensory evoked potential (EP) transient responses are then recorded from all electrodes while the subject is repeatedly exposed to a selected stimulus, e.g., a strobe light or a click generator or to a predetermined sequence of two alternate stimuli. Because the EP transient response is weak compared to the background steady-state brain electrical activity, the stimulus must be presented many times (e.g., 500) to the subject for later signal averaging. The total response period of interest is typically 1024 milliseconds, comprising 512 milliseconds before stimulus and 512 milliseconds after stimulus. The process is repeated for different stimuli.

Stimuli presented to the subject can range from simple flash, simple click, simple pattern reversal and simple somatosensory stimulation to those requiring complex decisions. Requiring a subject to discriminate between subtly different auditory stimuli (e.g., the words "tight" and "tyke") is useful in diagnosing dyslexia. This procedure is known as the Tight-Tyke evoked potential phenomic discrimination test. Picking an infrequently different stimulus from among other more frequent stimuli is useful evaluating subjects who have functional brain disorder.

Auditory stimuli generate a set of fast and a set of slow transient responses. The fast responses eminate from the brainstem and have a typical duration of 20 milliseconds. Brainstem responses are normally sampled for a total response period of 40 milliseconds comprising 20 milliseconds before stimulus and 20 milliseconds after stimulus. Filters 12 are adjusted to exclude frequencies below 300 Hz and to include frequencies up to 8000 Hz.

When EP transient responses from such stimuli are averaged to eliminate noise, two types of interference can occur. The first type, known as contingent negative variation (CNV), relates to the connection made by the brain between consecutive equally spaced stimuli when the subject is told to count the stimuli. The D.C. component of the resulting transient response shows a gentle dip and a sharp rise immediately before each stimulus, attributable to the subject's anticipation of the next stimulus. The sharp rise contaminates the evoked potential transient response and makes it difficult to establish a zero baseline. By including as part of the interval between stimuli a first pseudorandom time element which varies from 0 to a period longer than the post-stimulus response and is also a multiple of the wavelength of the interfering frequency described below, the CNV effect is greatly reduced.

The second type of interference results from the existence of background noise at certain characteristic frequencies, e.g., 10 Hz, which reflect prominent bands of steady-state brain wave activity. The major interfering frequency of a given subject may be determined by a spectral analysis of his background EEG signal. The interference problem is especially significant in adults with prominent alpha waves and children with prominent slow brain wave activity. By including in the time interval between stimuli a second pseudorandom time element whose period varies from zero to the wavelength of the major interfering frequency, the background noise can be substantially reduced in the averaging process.

The inclusion of a prestimulus period of recoding for each transient response permits an accurate baseline determination at a later stage of signal processing in order to establish a true zero level for the post-stimulus response and permits a determination of the quality of the signal averaging process.

Pseudorandom stimulus controller 9 measures the interval between stimuli as a combination of the post-stimulus response period, the first pseudorandom period described above, the second pseudorandom period described above, and the pre-stimulus response period.

Figure 31:
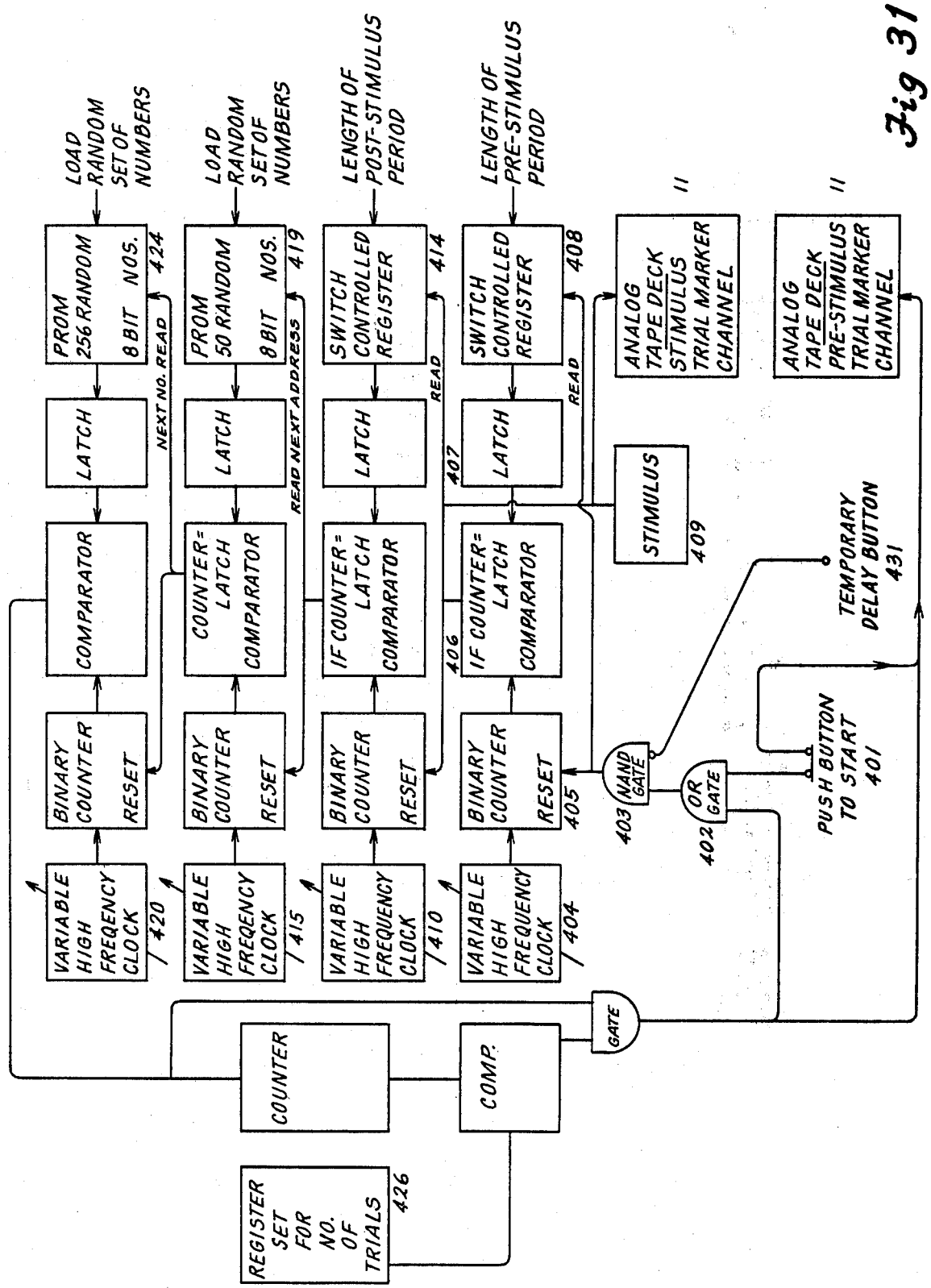
FIG. 31 is a block diagram of pseudorandom stimulus controller.

As illustrated in FIG. 31, pseudorandom stimulus controller 9 comprises a four-stage timer, each stage of which in turn measures one of the four periods included in the interval between stimuli. The first stage comparator 406 measures the pre-stimulus period $p_1/f_{c1}$ where $P_1$ is a number preset by the operator in register 408 and $f_{c1}$ is the frequency set on variable frequency clock 404. When the first stage timing is completed, the second stage times the post-stimulus period as $P_2/f_{c2}$ where $P_2$ is a number preset in register 414 and $f_{c2}$ is the preset frequency on clock 410. At the end of the first stage timing period, a stimulus trial marker (5 volt spike) is recorded on the trial marker channel of tape recorder 11 and stimulus 409 is triggered. The selected post-stimulus period is long enough to permit a full decay of the transient response being observed. At the end of the second stage timing period, the third stage measures the first pseudorandom time period $P_3/f_{c3}$, where $P_3$ is the next pseudorandom number in programmable read only memory (PROM) 419 and $f_{c3}$ is the preset frequency of variable clock 415. PROM 419 has been preloaded with a pseudorandom sequence of numbers. At the end of the third stage timing, the fourth stage measures a second pseudorandom period in an analogous manner based on a pseudorandom sequence in PROM 424 and a preset frequency on clock 420. When the fourth stage timing period is over, a pre-stimulus trial marker (5 volt spike) is recorded on the trial marker channel of recorder 11. A new timing cycle is then completed and the process is reiterated until the total number of transient responses recorded equals a preset number in register 426 or the process is stopped by the operator. The entire process is begun by pushing button 401, which causes the recording of a pre-stimulus trial marker. Temporary delay button 431 can be used to temporarily delay the continued operation of the timer at the operator's discretion, as for example when the subject is distracted in a manner which would render the transient response useless. A low order bit in PROM 424 or PROM 419 can be set to 0 or 1 by the operator for each number loaded into PROM 24 or PROM 19 so that two different stimuli (e.g., auditory and visual) can be triggered in a preselected order or pattern, with one stimuli being presented more frequently than the other.

The result of the recording session is an analog tape of raw EEG and EP voltage data and calibration voltages on 20 channels with trial markers on a twenty-first channel. The next step is to load the data into computer 13.

As previously described, brain electrical activity mapping software 28 performs data collection, data manipulation, and data display functions in accordance with central information provided by the operator. The various operations can be performed in any sequence and the operator can perform a series of functions iteratively. The operator provides control information through the keyboard of terminal 22 and receives information concerning the various operations on printer 23, waveform monitor 18 and topographic color monitor 20. The flexibility of operation heightens the system's utility as a diagnostic and analytical tool.

Data Loading

Under operator control, EEg data for each brain state and related calibration signals are loaded directly onto disk storage from recorder 11 after passing through filters 12 set to pass frequency components between 0.5 and 50 Hz or between 0.5 and 1000 Hz and epileptic spike data. Gain controls on the filters are adjusted to fully utilize the signal capacity of converters 15, 16. EEG data can be sampled at rates as high as 20,000 samples per second.

Under operator control, EP data is passed through filters 12 set to eliminate frequencies above a selected frequency of between 40 and 100 Hz, or below 300 Hz for brainstem data, and is signal averaged in core memory using core averaging operation 55, which automatically rejects bad data and sets the zero baseline.

Typically EP data is sampled every 4 milliseconds, or every microseconds for brainstem analysis, and 256 sampled are taken, 128 pre-stimulus and 128 post-stimulus. If the operator determines that the EP transient response data is very noisy, he may alternatively record the data as raw data and use raw data reduction operation 58 to average only selected transient response trials. In cases where the transient response data may not contain the necessary stimulus trial markers, such as in recordings of rapid eye movement (REM) sleep, the data can similarly be recorded as raw data and trial markers can be added manually by the operator, using raw data operation 58, before signal averaging is done.

Raw Data Quality Control and Display

To assure the maximum accuracy and utility of raw data, the operator can, using raw data quality control operations 56, display recorded waveforms, accept or reject each waveform for later processing, have mathematical smoothing operations performed, reset baselines or eliminate certain points of data.

The operator views the EP transient responses for the 20 channels for the purpose of evaluating the utility of each curve and specifying modifications which will improve their utility when displayed. The operator may direct a further adjustment of the baseline, which has already been set automatically, by having a constant number added to or subtracted from the value in each frame, or can determine to have the automatic baseline determination redone using a smaller number of the later pre-stimulus frames as the baseline. This procedure is particularly useful when the early pre-stimulus frames are found to contain the tail end of the transient response of the prior stimulus. By reviewing the relative levels of $V_{RMS}$ (pre-stimulus) and $V_{RMS}$ (post-stimulus) for a given channel, the operator can determine whether the background noise level is unacceptably large with respect to the transient response, necessitating another recording session with the subject. The operator may also filter any high frequency noise in the post-stimulus period by three-point interpolation.

As part of the raw data quality control process, if a channel contains spurious values (e.g., voltage spikes) in particular frames, the operator can eliminate those values and substitute values interpolated from the next prior and next later frames. If the voltage levels on one channel are substantially higher than for the other channels, the operator can flag that channel to indicate that the channel should be excluded from the subsequent display scaling procedure (described below). Based on the operator's instructions, the automatic baseline determination may be redone and the results are viewed again until the operator is satisfied that the set of transient responses contain satisfactorily low noise levels and are properly zeroed.

Raw data topographic display operation 57 enables the operator to display a cartoon series of topographic maps of raw data, which has been expanded by interpolation into a matrix of 128 × 128 points. The cartoon can be started or stopped and run forward or reversed at will. When raw EEG data is to be cartooned, the operator can sample the data at a high rate, e.g., 400 frames per second, and then display the information at slower speed or in a series of matrices, each of which is an average of a sequence of frames. The averaging can be done on a running basis, so that the first N frames are averaged and displayed, then the N frames beginning with the second frame are averaged and displayed, and so on.

EEG Data Reduction

Raw EEG data is converted to spectral data using the fast Fourier transform process of raw data operation 58, as previously described. The segments of raw EEG curves whose spectral data is averaged are generally about 2 seconds in length each, which is shorter than the average period between spurious artifact signals. Typically from 15 to 90 segments are spectrally analyzed and the spectra averaged. The spectra usually consist of 128 frequency bands of ½ Hz in width covering the spectrum from 0 to 64 Hz. The ends of each segment can be tapered in accordance with the operator's discretion in connection with the Fourier transform process.

Reduced Data Quality Control and Topographic Display

Working with reduced EP and EEG data, that is sequences of time frames of transient response data and groups of spectral band data, the operator can use reduced data quality control operation 59 to view the waveforms, discard bad data reflecting movement artifact, eye blink, or muscle activity and eliminate high frequency noise. The reduced data can then be topographically displayed on a frame by frame or cartooned basis using the reduced data topographic display operation 60. In either case, the operator can form frames which represent combinations of underlying frames. For example, groups of ½ Hz bandwidth frames can be combined into larger bandwidth frames corresponding with typical spectra of clinical interest, e.g., alpha, beta, delta and theta. Bands of any desired width can be formed. In addition to displaying raw spectral energy information from EEG data, it is possible to display normalized spectral energy in which the points on each display are normalized to the overall spectral energy of each electrode or to the average overall spectral energy at all electrodes. In the case of EP data, it is similarly possible to display each point as a normalized value to the value at one specific electrode, e.g., the vertex electrode designated "$C_z$", or to a standardized value, or to a selected value, or to the $V_{RMS}$ of the background activity at each electrode, or to the $V_{RMS}$ of all electrodes. Similarly, the 128 frames of an EP transient response can be grouped into frames of greater time duration for display.

Group Data Analysis

By accumulating a number of stored data frames, it is possible for the operator to assemble and display group data files using group file production operation 61 and group topographic data display operation 62.

Significance Probability Mapping (SPM)

Using stored data for various groups and individuals, the operator can perform and display topographically t-statistic comparisons between groups of frames and z-statistic comparisons between an individual frame and a group of frames. Any other statistical group comparison can also be used to form a display matrix to illustrate group differences. This type of analysis, significance probability mapping (SPM), enables the operator to identify significant brain activity features related to various neurophysiological illnesses and conditions.

Grid Sector Analysis

Frames produced by the SPM procedure may be further analyzed by a Grid Sector Analysis (GSA). While the frames produced by the SPM procedure reflect regional abnormalities, the GSA procedure produces numerical measures of the degree of global or focal deviations from normal, which can assist in automatic determination of the existence of regional abnormalities in unknown subjects.

The first step of the GSA process conceptually requires the division of a frame into a number of different grids, each divided into sectors of a uniform size. Within each grid sector, the mean of all values of the data points lying within the sector is determined as the value of that sector. The process is repeated for grids of different fineness. Preferably three grids, of 4000 sectors, 64 sectors, and 16 sectors respectively, are used. Histograms of sector values are then prepared for each grid reflecting sector t-statistic or z-statistic values on the horizontal axis and numbers of sectors having that value on the vertical axis for each grid. Various analyses of the histrograms, which differ for focal and global abnormalities, will indicate whether an abnormality is focal, i.e., localized in one area, or global, i.e., diffused over a large part of the brain. One such analysis would simply be the observation that the peak number of sectors for the coarser grids will be at lower z or t values in the case of a global abnormality than in the case of a focal abnormality.

In the case of focal abnormalities, there is a marked difference in the histograms for the three grids, while in the case of global abnormalities, there is little or no difference for the three grids. A variety of features can be developed from the histograms to serve as possible diagnostic rules. The maximum z-value for each grid, the maximum amount of asymmetry between homologous grid regions, the mean asymmetry between homologous grid regions, and the difference between the absolute values of the sum of all left hemisphere and all right hemisphere values. Also, one can calculate the number of regions above certain criterion levels for each histogram.

A group of spectral maps or a series of EP responses can be analyzed as an ensemble by forming at each matrix point the mean of the values of each map in the ensemble. The grid region on each individual map showing the largest value is given a score of 4, the next largest a score of 2, the third largest a score of 1, and the rest a score of 0. The scores are then summed by region across all maps in the ensemble, and the regions having the three largest scores and their sum are stored as indications of focal features. The same process is repeated for the three regions having the greatest asymmetries in each image between corresponding grid sectors. The resulting information can serve as features which can be processed using TICAS to develop diagnostic rules to classify unknown subjects between a group of normals and a group having a particular dysfunction. The numerical descriptors generated by GSA, when used for statistical analysis are approximately as successful in the identification of patients with brain tumors as visual inspection of EEG data by expert clinicians.

Coefficient of Variation Analysis

Given an ensemble of segments of data, the operator can determine the mean and the standard deviation of each point across the segments. By displaying the standard deviations as percentages of mean at each point, the coefficient of variation (C/V) across the skull can be observed topographically. The normal expect range of C/V values is 40–60% and deviations from that range are immediately evident from the displays. The C/V display is useful in demonstrating head regions where there are wide variations in activity, e.g., epileptogenic regions.

Difference Maps

A display matrix can be formed to represent at each point, the difference in value of corresponding points on two underlying frames. This permits, for example, displays which suggest the regions of the brain activated by patterned light, by comparing the frames corresponding to plain light stimulation and to patterned light stimulation.

Automatic Diagnostic Rules

Working from significant brain activity features and using TICAS-related operations 65, 67, 68 and 69, the operator can develop and test diagnostic rules for accurately classifying unknown subjects between normal and abnormal groups.

Scaling

Several of the available BEAM system operations produce color topographic displays. Video monitor displays typically involve assigning to each point on the display a grey tone of color which represents the value of the point. Sixteen tones of color represent 16 different graduated values. For example, red can be used for positive values and blue can be used for negative values with the grey tone of blue or red indicating the level of positive or negative value. An absence of color represents zero. In order to maximize the visual effectiveness of the display, it is desirable to scale the values of the data points to the available color tone levels in such a way that the useful variations in value are spread among the maximum range of color tones. The scaling can be done according to a variety of options. The data points can be scaled so that the maximum absolute value of the data points over a set of matrices will be equivalent to the maximum positive and negative color tones and all other points will be scaled linearly to the intermediate color tones. Scaling can be done from zero to the maximum absolute value. The same scaling technique can be accomplished with one or more channels excluded by the operator from the scaling process so that unusually high value data points will not skew the scaling process. Scaling can be done on a matrix by matrix basis rather than across a group of matrices. Scaling can be done to a maximum value chosen by the operator. In the scaling process, any data value which is larger than the brightest available grey color will be truncated and displayed as that brightest color.

Three-Point Linear Interpolation

Since the data frames to be presented for display originally contain a relatively small number of points, e.g., 20 points, and the display is preferably of a continuous matrix of 128×128 points, expansion of the data by some form of interpolation is required. The expansion is accomplished by three-point linear interpolation, in which each display point is determined as a sum of the values of the three nearest data points on the original data frame, each multiplied by a predetermined coefficient which reflects the precise location of the display point. As an alternative to the software previously described, the calculation of the display point can be done on hardware having an extremely short processing time, making possible "real-time" displays, that is, each display matrix is calculated in a time shorter than the display time for each display matrix. A detailed description of the three-point interpolation technique is contained in U.S. patent application Ser. No. 221,830 (hereby incorporated by reference).

Display Features; Multidimensional Display

Figure 32:
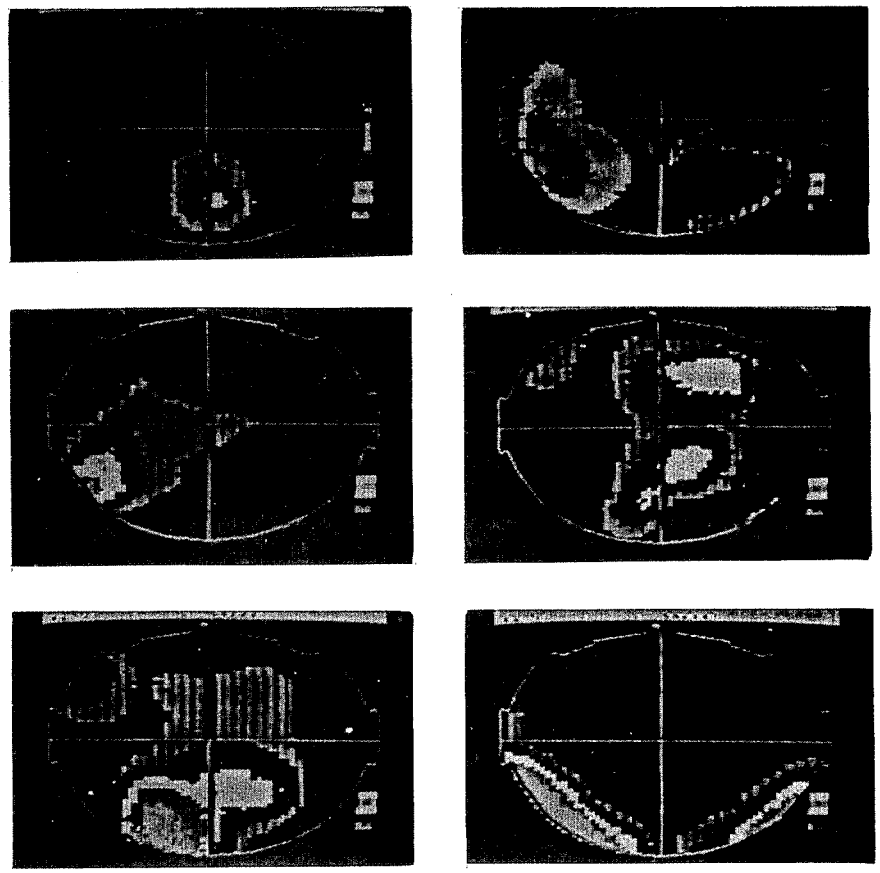
FIG. 32 is a sample of topographic displays generated by a brain electrical activity mapping system.

As illustrated in FIG. 32, the each topographic display comprises an outline of the skull with an indication of its orientation with respect to the ears and nose. All display points outside the outline are suppressed. Within the skull outline are displayed the grid of data points, each of which reflects a value or values for that point on the skull. The number of dimensions of information which may be represented by a given point varies with the display method. Frequently only one dimension of information is presented at any point in the form of a grey-tone of color on a predetermined grey-tone scale. Alternatively additional dimensions may be reflected at a point as a unique combination of three colors. Three dimensions can be represented by the quantity of each of the original colors which is mixed into the combination and a fourth dimension could be the lightness or darkness of the three. In this manner, for example, spectral EEG data for four frequency bands of brain activity could be displayed simultaneously. A detailed description of this four-dimensional display is contained in U.S. patent application Ser. No. 221,830.

Whenever displays are cartooned, the operator may select the frame rate of display from stationary to ten frames per second minimum. The cartoon can also be displayed legarithmically with time, so that the later matrices are displayed in faster sequence then the earlier ones, which visually compensates for the fact that more EP response information is available just after the stimulus than toward the end of the response period.

Examples of System Use

The brain electrical activity mapping system offers a powerful brain diagnostic and research tool by permitting immediate video display of information about steady-state brain waves, EP transient responses, spectral analyses of EEG signals, and statistical information based on these types of data, and the ability to develop diagnostic rules from selected features of data. The following examples illustrate the versatility and utility of the system.

Suspected Epilepsy

Although the "spike and wave" as seen on routine EEG graphs is virtually diagnostic of epilepsy, over 10% of all true epileptics fail to demonstrate this abnormality. Use of special electrodes, sleep studies, and activating drugs often fails to produce spikes in true epileptics. This means that although an epileptic may have brain cortex that is capable of demonstrating sufficient irritability at times to produce a seizure, that at other times it fails to be sufficiently irritative to produce a spike on the EEG and thus eludes diagnosis. Topographic display is of great assistance in such situations. Such suspected epileptic patients should have eyes open (EO) and eyes closed (EC) topographic studies performed. Irritative cortex presents itself as focal increases of activity over all frequency bands, especially the high frequency beta bands. The visual evoked EP response (VER) topographic study should also be performed. Irritative cortex leads to focal increases of both positive and negative waves. If the epilepsy is associated with an atrophic lesion, a region of reduced EEG and EP activity may be found in close association with the focal irritability.

When spikes are found, displays of their topographic extent are extremely useful in determining their point of origin. In this case, raw EEG data is displayed in cartoon form thus delineating the epileptic dipole.

Suspected Supratentorial Brain Lesion

Patients are often referred for EEG tests in order to rule in or out a lesion of one or both cerebral hemispheres. This includes tumor, stroke, abscess, atrophy, arterio-venous malformation, congenital malformation, hemorrhage, regional encephalitis. These subjects should be subjected to topographic studies in the eyes open and eyes closed brain states, and for the VER and bilateral somotosensory evoked response (BSER) EP situations. In general these lesions may be recognized by the pattern of hypo- or hyperactive cortex that become visible on the brain electrical activity mapping images. For example, tumors show decrease in activity early, excessive activities later, and reduced activity at the vertex. Brain electrical activity mapping greatly adds to the information obtained by radiographic scanning as it is sensitive to the functional disturbances produced by these lesions which usually extend beyond the anatomical limits of the lesion.

To pinpoint abnormalities the technique of significance probability mapping (SPM) should be used. Furthermore, quantification of a lesion by grid sector analysis (GSA) is often useful.

Brain electrical activity mapping is most useful when tests must be applied to a large population for screening purposes or repeatedly to a single person. Such uses would include screening for tumor and stroke, determining whether a lesion is increasing or decreasing, and assessing the effects of treatment on a lesion. Brain electrical activity mapping is completely non-invasive, and not dangerous as radiographic techniques would be in such circumstances. There is also evidence that many lesions produce electrical (functional) disturbances before they can be detected by radiographic means.

Suspected Learning Disabilities

Brain electrical activity mapping studies are most useful in the elucidation of regional abnormalities of brain activity found in dyslexia, hyperactivity, dyscalculia, and combinations of the above. For example, dyslexia reveals abnormalities not just in the classic left temporal lobe speech areas but in the medial frontal lobe bilaterally. To demonstrate these abnormalities, one needs to perform the full test battery which includes: right hemispheric activating tests (the Kimura Figures task and listening to music as described elsewhere); left hemispheric activating (listening to speech and reading Grey Oral passages as described elsewhere); and bi-hemispheral tests (Paired Associates test and the Tight-Tyke evoked potential phenomic discrimination test as described elsewhere).

Automated classification tests to discriminate among these clinical entities can be developed.

Emotional Dysfunction

Many forms of emotional disorder can be caused by the lesions mentioned above. Brain electrical activity mapping can be more useful in the recognition of covert pathology in this patient population than radiographic techniques. In addition, certain forms of psychopathology have recognizable brain electrical activity mapping signatures. For example sociopathic behavior is associated with lack of synchrony between the frontal lobes; e.g., the VER may show different electrical polarity between the right and left frontal lobes. Schizophrenia shows markedly increased EEG slow activity overlying the frontal regions. In this group of subjects, the eyes open and eyes closed EEG and VER studies are most useful.

Infant Competence

Discrimination between babies at risk for future learning and emotional problems is a frequent clinical request. Brain electrical activity mapping has proven useful in accomplishing such discrimination. In addition to studying the EEG and VER in stages 1 and 2 sleep, the EEG should be studied while the babies are brought into the alert state and maintained there as discussed elsewhere. Less competent babies, for example, show paradoxical increases in frontal delta slowing as they are alerted.

Suspected Dementia

Senile and pre-senile dementia represent a major problem for gerontologists and neurologists. Radiograpic evidence of brain abnormality may not be found until the clinical symptom complex is well established. On the other hand, brain electrical activity mapping studies demonstrate early abnormalities in a non-invasive manner. The best battery of tests is similar to those described above for suspected learning disabilities, but generally the tight-tyke EP is replaced by another EP where the subject must discriminate between frequently and infrequently heard tone pips of differing frequency. A difference EP between the response to the two different tone pips is produced. The topographic display of the difference EP shows a marked reduction in dementia and may be used to follow the course of dementia and the response of dementia to pharmacotherapies.

Headache

Headache may be caused by many factors. Brain electrical activity mapping is very useful to screen out serious lesions of the types described as supratentorial lesions above. The specific syndrome of migraine headache has a frequently seen pattern on brain electrical activity mapping of excessive 8-11 Hz occipital oscillations and excessive occipital activity. It is best to use the EO and EC EEG and VER for headache. Occasionally the BSEP is useful.

Comparison of Individual to Group

As described above, the brain electrical activity mapping system is generally able to compare an individual statistically to a group and display the result topographically. In a clinical setting, the individual in question, who may have displayed a normal CT scan, is compared to an age matched/sex matched group of normals, and abnormalities are then displayed in color-mapped form, wherein bright colors show high abnormality and dull colors show insignificant abnormality. This technique provides an effective diagnostic tool.

Comparisons of Groups; Automatic Diagnosis Rules

The result of a group comparision under the system is a topographic display of statistical difference expressed as t-statistics, which when coupled with the number of degrees of freedom available in the calculation, produce a probability level of significant difference between two groups at a particular brain state. For instance, a group of normals could be compared to a group of schizophrenics by the creation of t-statistic displays with respect to a variety of brain states and stimuli. The user looks for displays which exhibit high degrees of coherence and statistical difference. This is normally shown on a screen in color. The larger statistical differences appear as brighter colors. The degree to which the differences are focused at particular points or diffused over the skull is also apparent. Smoothness in the lines dividing areas of different brightness suggests focused differences, while diffuse differences are suggested by ragged edges between dim and bright areas. It is possible for the researcher, upon selection of a particular map that shows something interesting, to save the matrix for later analysis. Such a saved matrix of t-statistics can be used to non-linearly weight the underlying data frames to create features which can be analyzed using TICAS. Once a set of saved frames representing group difference information is accumulated, he then converts all of the saved information, representing features which tend to distinguish the two groups into a file format which is suitable for analysis by TICAS, which is a multi-variate classification system, publicly available from the University of Arizona, courtesy of Dr. Peter H. Bartell.

TICAS is designed to sift through all of the features saved in the course of the inter-group analysis and pick those which prove to be the most discerning mathematically to produce a set of features which succinctly allows automatic diagnosis of a patient.

This procedure has been used to successfully discriminate between normal subjects and those with dyslexia, to discriminate between normal subjects and those with supertentorial brain tumor, and to discriminate between subjects with exposure to organophosphate compounds and nonexposed controls.

Dyslexia Analysis

An article, *Dyslexia Regional Differences in Brain Electrical Activity by Topographic Mapping*, Duffy et al. (Annals of Neurology, Vol. 7, No. 5, May, 1980), hereby incorporated by reference, describes the use of the brain electrical activity mapping system to identify the parts of the brain whose electrical activity differs for individuals suffering from reading disability (dyslexia) as compared with normal individuals, and to establish objective standards for diagnosing dyslexia. The previously described battery of brain state tests were administered to a dyslexic group and a control group. Visual and auditory stimuli were repeatedly presented to both groups and recorded with the appropriate trial markers. The stimuli were offered in pseudorandom fashion. Using the brain electrical activity mapping system, topographic displays of the alpha (8 to 11.75 Hz) and theta (4 to 7.75 Hz) activity at each electrode for each tested brain state for each subject were produced. Similar cartoons of 128 frames (4 milliseconds each) were prepared for each type of EP response for each subject. The resulting brain state frames and EP response frames for the dyslexic group and the control group were then averaged to form mean frames of each group for each state and stimulus. The two groups of mean images were then compared using the t-statistic function. A further transformation produced a matrix of percentile index values (PI) whose value is related inversely to t-values. The PI values permit a graphic localization of regions of maximum difference between the dyslexic group and the control group. By topographically displaying the PI matrices for alpha and theta for each brain state and for each EP stimulus, it was possible to identify the brain regions which differed between the dyslexics and the controls. As a final step, a new display matrix was formed which summarized the differences reflected in all of the PI matrices as indicated by the occurrence of a certain PI level on at least one of the underlying PI matrices. The map of PI differences having a value of at least 2 identified four brain areas related to dyslexia: (1) bilateral medical frontal, (2) left anteriolateral frontal, (3) left mid-temporal and (4) left posterolateral quadrant. Classic concepts of dyslexia had not suggested the involvement of all of these brain areas in dyslexics. The study also indicated that alpha brain activity was involved in dyslexia as well as the theta activity which has previously been viewed as of primary importance.

In *Dyslexia: Automated Diagnosis by Computerized Classification of Brain Electrical Activity*, Duffy et al. (Annals of Neurology, Vol. 7, No. 5, May, 1980) hereby incorporated by reference, specific highly effective diagnostic rules for identifying dyslexics were developed by a rule selection process applying TICAS software to the brain wave data derived in the study described immediately above. Working from displays of brain electrical activity, 183 features were identified for particular regions and brain states in which the strongest differences between the dyslexic group and the normal group occurred. Two of the 183 features were identified as capable of classifying unknown subjects as dyslexic or normal with a success of 80-90%.

Localization of Tumor

In *Brain Electrical Activity Mapping (B.E.A.M.); A Method for Extending the Clinical Utility of EEG and Evoked Potential Data*, Duffy, et al (Annals of Neurology, Vol. 5, No. 4, April, 1979), hereby incorporated by reference, the use of brain electrical activity mapping system topographic displays to identify the location of a brain tumor was discussed. Spectral EEG data in the four classic bands (delta, theta, alpha, and beta) was recorded for various tested brain states. Average EP response data for strobe light stimuli comprising 128 time frames of 4 milliseconds each was also recorded. After three-point linear interpolation to expand the matrix, displays of spectral EEG data, and cartooned EP data were obtained. FIG. 5 of the article illustrates the spectral EEG displays in the four classic bands of brain activity for a patient with a known tumor, which had been located by CT scanning. The assymmetries in the spectral displays also identify the area of the tumor, although the suggested lesion size was larger than indicated by CT scanning. Analysis of 7 tumor patients, whose classic EEG's were normal or non-localizing, showed that brain electrical activity mapping studies were able to define the lesions almost as effectively as CT scan.

Use of Significance Probability Mapping with B.E.A.M. to Compare Groups and Compare Individuals to Groups In *Significant Probability Mapping: An Aid in the Topographic Analysis of Brain Electrical Activity*, Duffy et al., accepted for publication the authors describe the use of topographical displays of statistical transformations of data. In one application, EP response data was obtained from a group of subjects with brain tumors and a second control group of subjects. The data was broken into sequential frames of 4 milliseconds each. For the control group, new matrices of mean and variance of each electrode over all members of the group were prepared. A z-statistic matrix was formed for each tumor subject to illustrate his deviation from the normal population. Using the z-statistic display a clinical neurophysiologist was able to identify 11 of 12 tumor subjects.

In a second application, discussed in the same article, EEG steady-state signals were recorded for three different brain states (resting but alert with no external stimulation, listening to a tape recording of speech, and listening to a tape recording of music) for individuals in a group of dyslexics and individuals in a group of normal readers. Matrices of alpha band activity were produced for each individual, and mean and variance matrices for each state were prepared for each of the two groups. For each group t-statistic matrices were formed to compare the resting and listening to speech states and the resting and listening to music states. By examining the t-statistic displays for the two groups it was possible to infer the differences in speech-induced and music-induced brain activity between the dyslexics and the normal readers. Those determinations could not have been made from an analysis of the underlying EEG alpha matrices.

Use of Grid Sector Analysis of B.E.A.M. SPM Data to Determine Degree of Focal or Global Deviation From Normal In an unpublished article, "Quantification of Focal Abnormalities in BEAM Data by Grid Sector Analysis: Automated discrimination Between Normal Subjects and Patients with Supratentorial Brain Tumor", Duffy, et al., describes uses of grid sector analysis as part of the brain electrical activity mapping system for the purpose of automated neurophysiological diagnosis of brain tumor. In this application, EEG and visual EP data were recorded from a group of patients with confirmed supratentarial brain tumor and from a control group. SPM matrices were prepared comparing the tumor subjects to a normal group and comparing the control group to the tumor group. Four 96 millisecond time periods of EP data were analyzed. Grid sector analyses on the data resulted in a set of 1096 combined global and focal features from the combined EEG and EP data. By a process of features selection and rule development and testing, two features were identified as most useful in distinguishing the tumor subjects from the control subjects. When classification rules developed on the initial group of 30 subjects were applied to a new group of 10 subjects, containing 5 normals and 5 subjects with brain tumor, all ten were correctly classified.

Other Embodiments

Other embodiments of the invention are within the following claims. For example, the input data may be obtained from any type of transducer capable of measuring brain electrical activity, and topographic displays can be prepared from the signals taken from the skull, without interpolation of additional points to form a display matrix.

Related Applications

This application is related to the following applications, each of which is hereby incorporated by reference:

(1) Frank H. Duffy, Brain Electrical Activity Mapping (BEAM)
(2) Norman David Culver, Brain Electrical Activity Mapping (BEAM)
(3) Norman David Culver, Analysis of Brain Electrical Activity
(4) Norman David Culver, Apparatus and Method for Topographic Display of Multichannel EEG Data, U.S. Ser. No. 221,830.

What is claimed is:

1. Apparatus for generating a topographic display of information on the electrical activity of the brain, said apparatus comprising
   a plurality of electrical-activity transducers adapted to be placed at spaced apart locations on the skull of a patient,
   stimulus means for repeatedly providing a sensory stimulus for activating the brain to produce EP responses to said transducers,
   response averaging means connected to be responsive to said transducers, to produce average responses for each transducer,
   processing means connected to be responsive to said averaging means for processing said average responses to generate a time sequence of matrices,
   display means connected to be responsive to said processing means, for displaying said matrices as a time sequence of topographic maps of the skull, said matrice having elements defining discrete points of said maps,
   said display means including means for displaying said topographic maps at a variable frame rate, said maps corresponding to different portions of said average responses being displayed respectively at different selected frame rates.

2. The apparatus of claim 1 wherein said display means includes means for displaying maps corresponding to initial portions of said average responses at a slower rate than maps corresponding to later portions of said average responses.

3. The apparatus of claim 1 wherein said display means includes means to display said topographic maps at a frame rate that varies logarithmically.

4. Apparatus for generating a topographic display of information on the electrical activity of the brain, said apparatus including
   a plurality of electrical-activity transducers adapted to be placed at spaced apart locations on the skull,
   processing means connected to be responsive to said transducers, for processing responses of said transducers to generate a time sequence of matrices, each of said matrices having elements representing the instantaneous amplitudes of said responses at various locations on the skull and there being a sufficient number of said matrices for a selected time period of actual brain activity for capturing onset of a transient event that occurs with a rapidity on the order of that of an epileptic spike,
   said processing means including means to generate from said time sequence of matrices a running-average matrix which at any given time represents the current matrix averaged with a selected number of the matrices preceding it in time,
   display means connected to be responsive to said processing means, for displaying said matrices as a time sequence of topographic maps of the skull, said elements defining discrete points of said matrice having maps,
   said display means including means for displaying said topographic maps at a variable frame rate and for selectably slowing said frame rate to permit observation of said transient event.

5. The apparatus of claim 4 wherein said processing means includes means for generating 200 or more matrices for each second of real time.

6. Apparatus for generating a topographic display of information on the electrical activity of the brain, said apparatus comprising
   a plurality of electrical-activity transducers adapted to be placed at spaced apart locations on the skull of a patient,
   storage means connected to be responsive to said transducers for storing responses of said transducers during first and second time periods,
   processing means connected to be responsive to said transducers, for processing said responses to generate first and second matrices each having elements representing brain activity at different skull locations, said first matrix representing information on brain activity during said first period, and said second matrix representing information on brain activity during said second period,
   different means connected to be responsive to said processing means, for forming a difference matrix having elements each corresponding to the difference between corresponding elements of said first and second matrices,
   display means connected to be responsive to said different means, for displaying said different matrix as a topographic map of the skull, said matrix elements each forming a discrete point of said topographic map.

7. The apparatus of claim 6 further comprising stimulus means for providing a sensory stimulus to generate an EP response and wherein at least one of said first and second periods of time are during said EP response.

8. Apparatus for generating a topographic display of information on the electrical activity of the brain, said apparatus comprising
   a plurality of electrical-activity transducers adapted to be placed at spaced apart locations on the skull of a patient,
   stimulus means for repeatedly generating a sensory stimulus for the brain, to produce at said transducers repeated segments of data, each said segment having a pre-stimulus response and a post-stimulus response,
   response averaging means connected to be responsive to said transducers, for averaging said segments to produce average pre-stimulus and average post-stimulus responses for each transducer,
   baseline means connected to be responsive to said responsive averaging means, for determining a zero baseline for said average segments from the mean level of at least a portion of the respective average pre-stimulus response, and subtraction means connected to be responsive to said baseline means, for generating zeroed average segments by subtracting from each average segment the zero baseline determined by said baseline means, processing means connected to be responsive to said subtraction means, for processing said zeroed average segments to generate one or more matrices, each said matrix having element representing information on the electrical activity of the brain at one location on the skull, display means connected to be responsive to said processing means, for displaying said one or more matrices as topographic maps of the skull, said matrix elements forming discrete points of said maps.

9. The apparatus of claim 8 further comprising means connected to be responsive to said stimulus means, for storing the time of occurrence of each said stimulus and means connected to be responsive to said means for storing, for dividing each said segment into a predetermined pre-stimulus subinterval during which the pre-stimulus response occurs and a predetermined post-stimulus subinterval during which the post-stimulus response occurs, by using said stored times of stimuli occurrence as an indication of the boundary between said subintervals.

10. The apparatus of claim 8 wherein said processing means includes means to generate from said zeroed average segments a time sequence of said matrices, the display elements of each matrix representing the instantaneous amplitude of an EP response at various locations on said skull, and said display means includes means for displaying said matrices in sequence, to thereby display said EP response as a time-varying topographic map.

11. The apparatus of claim 10 wherein said processing means includes means to generate said sequence of matrices in an endless loop, to thereby produce a cyclical display of said EP response.

12. The apparatus of claim 8 further comprising sampling means connected to be responsive to said transducers, for sampling and storing as a sequence of digital words said segments, and wherein said response averaging, baseline, and subtraction means all include means for performing the respective functions digitally.

13. The apparatus of claim 12 wherein said response averaging means includes a summing buffer connected to be responsive to said sampling means, and having locations for storing each said sampled digital word for each transducer and means connected to be responsive to said sampling means, for adding to said buffer locations new digital words corresponding to each new segment, to thereby generate said average pre- and post-stimulus responses.

14. The apparatus of claim 13 wherein said sampling means includes means for taking from 20 to 2000 equally-spaced-in-time samples of said pre-stimulus response and for taking 20 to 2000 equally-spaced-in time samples of said post-stimulus response.

15. The apparatus of claim 13 further comprising means connected to be responsive to said sampling means, for comparing said new digital words to predetermined limits and rejecting digital words falling outside said limits, thereby not adding said words to said buffer locations.

16. The apparatus of claim 12 further comprising means connected to be responsive to said transducers, for filtering high-frequency components from the post-stimulus response for any selected transducer by multipoint interpolation of the digital words for the selected response.

17. The apparatus of claim 8 wherein said baseline means includes means for selectively eliminating from the mean level computation portions of an average pre-stimulus response for a selected transducer, to thereby provide a more accurate baseline for the response of the selected transducer.

18. The apparatus of claim 8 further comprising means connected to be responsive to said baseline means, for displaying said pre-stimulus and post-stimulus responses and said baseline for a selected transducer, to permit an operator to evaluate the appropriateness of said baseline.

19. The apparatus of claim 8 wherein said baseline means includes means for calculating the root mean square average value of the average pre-stimulus response and of the average post-stimulus response and said display means includes means for displaying said root mean square average values along with said responses, whereby such root mean square value can be used in connection with said displayed responses to evaluate whether the noise level in the responses for any particular transducer is unacceptably large and for thereby determining whether new data should be taken.

20. The apparatus of claim 8 or 19 further comprising means connected to be responsive to said baseline means, for an operator to adjust the baseline value up or down for any selected transducer average response.

21. The apparatus of claim 8, 18, or 20 further comprising means connected to be responsive to said baseline means, for repeating the steps of calculating said baseline and viewing said responses for selected transducers, whereby adjustments can be made to said baseline until said responses are satisfactory.

22. Apparatus for generating a topographic display of information on the electrical activity of the brain, said apparatus comprising a plurality of electrical-activity transducers adapted to be placed at spaced apart locations on the skull of a patient or measure the EEG response at said locations, sampling means connected to be responsive to said transducers, for sampling said EEG responses during time intervals shorter than the anticipated interval between interruptions in the state of brain activity, spectral processing means connected to be responsive to said sampling means, for computing, for each of said transducers, the Fourier transforms of the sampled EEG responses and for computing from said Fourier transforms, for each of said transducers, the spectral energy contained in selected frequency bands, processing means connected to be responsive to said spectral processing means, for processing the output of said spectral processing means to generate a plurality of matrices, one said matrix for each selected frequency band, each said matrix having elements each of which represents the spectral energy within the respective frequency band at one location on the skull, display means connected to be responsive to said processing means, for displaying said matrices as topographic maps of the skull, said matrix elements forming discrete points of said maps.

23. The apparatus of claim 22 wherein said sampling means is arranged for sampling and storing as a sequence of digital words selected portions of said EEG responses, and wherein said spectral processing means includes means for digitally performing said Fourier transform determination.

24. The apparatus of claim 23 wherein said sampling means includes means to sample said EEG responses at at least 3 times the highest frequency in said selected frequency bands.

25. The apparatus of claim 24 wherein said sampling means includes means to sample said EEG responses at from 4 to 5 times said highest frequency.

26. The apparatus of claim 22 wherein said sampling means includes marking means for storing the start and stop times of a particular brain activity.

27. The apparatus of claim 22 wherein a time maximum interval for sampling said EEG responses is on the order of two seconds.

28. The apparatus of claim 22 wherein said sampling time interval of said EEG responses is from 0.1 to 4.0 seconds long.

29. The apparatus of claim 22 further comprising averaging means connected to be responsive to said spectral processing means, for averaging said Fourier transforms to generate, for each transducer, the average spectral energy contained within said frequency bands.

30. The apparatus of claim 22 wherein said frequency bands comprise the alpha, beta, delta, and theta bands.

31. The apparatus of claim 22 further comprising filtering means connected to be responsive to said transducers, for removing from said EEG responses frequency components outside the prominent frequency bands of brain electrical activity.

32. The apparatus of claim 31 wherein said filtering means includes means for removing from said EEG responses at least frequency components below 0.5 Hz and above 50 Hz.

33. The apparatus of claim 31 wherein said filtering means includes means for removing from said EEG responses at least frequency components below 0.5 Hz and above 1000 Hz.

34. The apparatus of claim 31 wherein said filtering means includes means for removing from said EEG responses at least frequency components below 300 Hz and above 5000 Hz.

35. The apparatus of claim 22 wherein said spectral processing means includes means for tapering the beginning and end portions of said responses prior to determination of the Fourier transform to reduce high frequency artifacts.

36. Apparatus for generating a topographic display of information of the electrical activity of the brain, said apparatus comprising a plurality of electrical-activity transducers adapted to be placed at spaced apart locations on the skull of a patient, processing means connected to be responsive to said transducers, for processing electrical responses measured at said transducers, said processing means including means for generating one or more matrices, each matrix containing a plurality of elements, said elements representing information on the electrical activity of the brain at particular skull locations, statistical processing means connected to be responsive to said processing means, for processing at least two said matrices to generate a statistical comparison matrix having elements, each element being representative of a statistical difference between the corresponding elements in said two matrices, display means connected to be responsive to said statistical processing means, for displaying said statistical comparison matrix as a topographic map of the skull, said matrix element forming discrete points of said map.

37. The apparatus of claim 36 further comprising interpolation means connected to be responsive to said statistical processing means, for expanding said statistical comparison matrix to a larger matrix prior to display, and larger matrix having additional statistical comparison elements for skull locations intermediate said transducer locations, said additional elements being generated by interpolation from the elements of said statistical comparison matrix.

38. The apparatus of claim 36 further comprising interpolation means connected to be responsive to said processing means, for expanding said matrices to larger matrices prior to said statistical processing, said larger matrices having additional elements for skull locations intermediate said transducer locations, said additional elements being generated by interpolation from the elements of said matrices.

39. The apparatus of claim 36 wherein said statistical processing means includes means to generate as said statistical comparison matrix a matrix of t values representing the statistical difference between a first and a second group of matrices, each group having matrices having a plurality of elements.

40. The apparatus of claim 39 wherein said statistical processing means includes means connected to be responsive to said means to generate a matrix of t values, for generating a first mean-value matrix having elements which are representative of the mean values of the respective elements the matrices said first group, means connected to be responsive to said means to generate a matrix of t values, for generating a first standard-deviation matrix having elements which are representative of the standard deviations of the respective elements of the matrices of said first group, means connected to be responsive to said means to generate a matrix of t values, for generating a second mean-value matrix having elements which are representative of the mean values of the respective elements of the matrices of said second group, means connected to be responsive to said means to generate a matrix of t values, for generating a second standard-deviation matrix having elements which are representative of the standard deviations of the respective elements of the matrices of said second group, means connected to be responsive to said means to generate a matrix of t values, for generating said matrix of t values from said first and second mean-value matrices and said first and second standard-deviation matrices.

41. The apparatus of claim 36 wherein said statistical processing means includes means to generate as said statistical comparison matrix a matrix of z values representing the statistical difference between one matrix and a group of matrices.

42. The apparatus of claim 41 wherein said statistical processing means includes
   means connected said means to generate a matrix of z values, for generating a first matrix representative of the mean of said group of matrices,
   means connected said means to generate a matrix of z values, for generating a second matrix representative of the standard deviation of said group of matrices,
   said matrix of z values being generating from said one matrix and said first and second matrices, each of said matrices having a plurality of elements.

43. The apparatus of claim 42 wherein said first matrix is representative of the mean of a normalized reference population, said second matrix is representative of the standard deviation of said population, and the elements of said matrix of z values are thereby representative of the number of standard deviations by which the elements of said one matrix differ from the mean of said population.

44. The apparatus of claim 36 further comprising
   means connected to be responsive to said statistical processing means, for producing from said statistical comparison matrix one or more quantitative features which are each determined by processing the elements within selected regions of said statistical matrix,
   means connected to be responsive to said means for producing features, for determining a statistical merit value for selected features,
   means for determining how to combine said features to form decision rules, and
   means connected to be responsive to said means for determining, for classifying individuals using said decision rules.

45. Apparatus for generating a topographic display of information on the electrical activity of the brain, said apparatus comprising
   a plurality of electrical-activity transducers adapted to be placed at spaced apart locations on the skull of a patient,
   statistical processing means connected to be responsive to said transducers, for processing responses at said electrical-activity transducers to generate a coefficient-of-variance matrix, said matri having element each of which represents the normalized standard deviation of the responses at one skull location, the normalized standard deviation being the standard deviation divided by the mean,
   display means connected to be responsive to said statistical processing means, for displaying said coefficient-of-variance matrix as a topographic map of the skull, thereby providing a map of the level of variation in brain activity.

46. Apparatus for generating a topographic display of information on the electrical activity of the brain, said apparatus comprising
   a plurality of electrical-activity transducers adapted to be placed at spaced apart locations on the skull of a patient,
   processing means connected to be responsive to said transducers, for generating from responses measured at said transducers a time sequence of first matrices, each said first matrices having display elements representing the instantaneous response at various locations on said skull,
   temporal interpolation means connected to be responsive to said processing means, for generating by interpolation second matrices interspersed in said sequence of first matrices, said second matrices having elements representing the approximate response at instants of time intermediate the instants of time associated with said first matrices,
   display means connected to be responsive to said processing means, for displaying said first matrices and said interspersed second matrices as a time sequence of topographic maps of the skull, said matrix elements forming discrete points of said maps, said second matrices enhancing the visual smoothness of the transitions over time between said first matrices.

47. Apparatus for generating a topographic display of information on the electrical activity of the brain, said apparatus comprising
   a plurality of electrical-activity transducers adapted to be placed at spaced apart locations on the skull of a patient,
   processing means connected to be responsive to said transducers, for generating one or more matrices from the responses measured at said transducers, each matrix having elements representing information on electrical activity of the brain at one location on the skull,
   display means connected to be responsive to said processing means, for displaying said matrices as topographic maps of the skull, said matrix elements forming discrete points of said maps,
   waveform quality control means for previewing said transducer responses or processed versions thereof, said quality control means including at least two of the following means
   means for tagging a response with information on its waveform quality, including an indication of whether the response should be used in later processing,
   means at the discretion of the operator for eliminating a response from further processing,
   means for automatically eliminating a response from further processing if a portion thereof exceeds a predetermined threshold,
   means for smoothing a response to eliminate undesired high frequency components,
   means for adjusting a zero baseline of a response, said zero baseline having been previously set automatically,
   means for eliminating selected portions of a response from further processing, and
   means for displaying in numerical form the value of a response at a point in time selected by the operator.

48. Apparatus for generating a topographic display of information on the electrical activity of the brain, said apparatus comprising
   a plurality of electrical-activity transducers adapted to be placed at spaced apart locations on the skull of a patient,
   means connected to be responsive to said transducers, for sampling responses measured at said transducers and storing the sampled responses as a series of data matrices, one matrix for each sampling time, means connected to be responsive to said means for sampling, for selectively viewing the sampled responses corresponding to a single transducer as a plot of transducer output versus time, quality control means for adjusting portions of said selectively viewed responses or eliminating said responses from further processing, processing means connected to be responsive to said means for sampling, for processing said data matrices to generate one or more processed matrices, said processed matrices having elements each corresponding to one transducer location, interpolation means connected to be responsive to said processing means, for generating expanded matrices by expanding the number of elements in said processed matrices to provide elements corresponding to skull locations intermediate said transducer locations, display means connected to be responsive to said interpolation means, including a video monitor capable of generating a matrix of grey tones for displaying said expanded matrices as topographic maps of the skull, said expanded matrices having elements defining the grey tones of discrete points on said maps.

49. The apparatus of claim 48 further comprising matrix storage means connected to be responsive to said means for sampling, processing means, and interpolation means, for tagging selected data, processed, or expanded matrices and storing them for later recall and processing.

50. The apparatus of claim 48 further comprising means connected to be responsive to said transducers, for storing calibration responses from said transducers and means for calibrating said responses matrices by determining from said stored calibration responses a DC offset and gain for each said transducer.

51. Apparatus for generating a topographic display of information on the electrical activity of the brain, said apparatus comprising a plurality of electrical-activity transducers adapted to be placed at spaced apart locations on the skull of a patient, processing means connected to be responsive to said transducers, for processing responses measured at said transducers to generate one or more matrices, each matrix having elements representing information on brain activity at different skull locations, display means connected to be responsive to said processing means, for displaying said one or more matrices as topographic maps of the skull, said matrix elements forming discrete points of said maps, said display means including a video monitor which generates a visible grey tone at each said discrete point, said tone being variable from a maximum tone to a minimum tone, and scaling means connected to be responsive to said processing means, for scaling said matrix elements to the available tones.

52. The apparatus of claim 51 wherein
said video monitor generates a zero tone intermediate said maximum and minimum tone and
said scaling means comprises at least two of the following means means connected to be responsive to said processing means, for scaling the maximum matrix element to the maximum tone and the minimum matrix element to the minimum tone and linearly interpolating inbetween, means connected to be responsive to said processing means, for scaling the maximum matrix element to the maximum tone and the minimum matrix element to the zero tone and linearly interpolating inbetween, means connected to be responsive to said processing means, for scaling the maximum matrix element to an operator supplied tone, means connected to be responsive to said processing means, for scaling the minimum matrix element to an operator supplied tone, means connected to be responsive to said processing means, for excluding from the scaling operation selected unusually high or low valued matrix elements and for assigning to matrix elements that fall outside the available tone range the closer of the maximum or minimum tone.

53. The apparatus of claim 51 wherein said video monitor generates colored grey tones of a first and a second color, with grey tones of said first color forming said grey tones between said maximum tone and said zero tone, with grey tones of said second color forming said grey tones between said minimum tone and said zero tone, and with the absence of a color tone forming said zero tone.

54. The apparatus of claim 53 wherein said two colors are complementary colors.

55. The apparatus of claim 53 wherein there are at least 6 grey tones of each of said two colors.

56. The apparatus of claim 51 wherein there are a plurality of said matrices to be displayed and said scaling means includes means for independently performing said tone scaling for each matrix displayed.

57. The apparatus of claim 51 wherein there are a plurality of said matrices to be displayed and said scaling means includes means for scaling with respect to the display elements in all said matrices so that the scaling remains the same for each matrix displayed.

58. The apparatus of claim 51 further comprising preview means connected to be responsive to said transducers, for viewing selected segments of the transducer responses and for tagging selected segments for exclusion from the scaling operation and wherein said scaling means includes means for identifying the presence of said tagging and for excluding data so tagged from said scaling operation.

59. Apparatus for generating a topographic display of information on the electrical activity of the brain, said apparatus comprising a plurality of electrical-activity transducers adapted to be placed at spaced apart locations on the skull of a patient, processing means connected to be responsive to said transducers, for processing responses measured at said transducers to generate one or more matrices, each matrix having elements representing information on brain activity at different skull locations, display means connected to be responsive to said processing means, for displaying said one or more matrices as a topographic map of the skull, said matrix elements forming discrete points of said map, said display means including a video monitor which generates a tone at each said discrete point, said tone varying from a maximum tone to a minimum tone, normalizing means connected to be responsive to said processing means, for normalizing said matrix elements to a selected value, and scaling means connected to be responsive to said processing means, for scaling said matrix elements to the available tones, said scaling means including means for assigning a selected tone to said selected normalization value.

60. The apparatus of claim 59 wherein said normalizing means includes means for normalizing said matrix elements to the matrix element representing brain electrical activity at the vertex.

61. The apparatus of claim 59 wherein said normalizing means includes means for normalizing each individual matrix element to the root mean square value of the background electrical activity at the skull location represented by the individual matrix element.

62. The apparatus of claim 59 wherein said normalizing means includes means for normalizing said matrix elements to the average root mean square value of the background electrical activity over all skull locations.

63. The apparatus of claim 59, 60, 61 or 62 further comprising stimulus means for repeatedly providing a sensory stimulus for the brain, to produce repeated EP responses at said transducers, response averaging means connected to be responsive to said transducers, for averaging said repeated responses for each transducer to produce an average response for each transducer, and wherein said processing means includes means for generating from said average responses a time sequence of said matrices, and said display means includes means for displaying said matrices in sequence.

64. The apparatus of claim 59 wherein there is further provided spectral processing means connected to be responsive to said transducers, for computing the Fourier transforms of the responses measured by said electrical-activity transducers and for computing from said Fourier transforms the spectral energy contained in selected frequency bands, said processing means includes means for processing the output of said spectral processing means to generate a plurality of matrices, one said matrix for each selected frequency band, each matrix having elements representing the spectral energy within the selected frequency band at various locations on the skull, and said normalizing means includes means to normalize said matrix elements either to the total spectral energy for all said frequency bands at the skull location corresponding to said matrix element or to the average total spectral energy for all said frequency bands for all matrix elements.

65. The apparatus of claim 1, 4, 6, 8, 22, 45, 46, 47, 48, 51, or 59 wherein said processing means includes interpolation means for generating by interpolation additional matrix elements for skull locations intermediate the locations of said transducers.

66. The apparatus of claim 65 wherein said interpolation means includes means for computing the values of said additional matrix elements by three point interpolation from the values associated with the three closest transducer locations.

67. The apparatus of claim 66 wherein said three point interpolation is linear.

68. The apparatus of claim 1, 4, 6, 8, 22, 36, 45, 46, 47, 48, 51, or 59 wherein the number of said electrical-activity transducers is in the range of 10 to 200 and the number of elements in said topographic maps is at least 5 times the number of transducers.

69. A method for generating a topographic display of information on the electrical activity of the brain, said method comprising the steps of placing a plurality of electrical-activity transducers at spaced apart locations on the skull of a patient, storing responses of said transducers during first and second time periods, processing said responses to generate first and second matrices each having elements representing brain activity at different skull locations, said first matrix representing information on brain activity during said first period, and said second matrix representing information on brain activity during said second period, forming a difference matrix having elements each corresponding to the difference between corresponding elements of said first and second matrices, and displaying said difference matrix as a topographic map of the skull, said matrix elements each forming a discrete point of said topographic map.

70. The method of claim 69 further comprising the step of providing as a stimulus for the brain during said first period a source of patterned light and providing as a stimulus for the brain during said second period a source of nonpatterned light.

71. A method of generating a topographic display of information on the EP response of the brain, said method comprising the steps of:

placing a plurality of electrical-activity transducers at spaced apart locations on the skull of a patient, repeatedly providing a sensory stimulus for the brain so as to produce at said transducers repeated segments of data, each segment including a pre-stimulus response and a post-stimulus response, averaging the repeated segments to produce an average segment for each transducer, determining a zero baseline for each average segment from the mean level of at least a portion of the average pre-stimulus response, subtracting the zero baselines from the respective average segments to produce zeroed average segments, processing the zeroed average segments to generate one or more matrices of elements, with each matrix element representing information on the EP response at one location on the skull, and displaying said one or more matrices as topographic maps of the skull, with each display point forming a discrete point on said maps.

72. A method for generating a topographic display of information on the electrical activity of the brain, said method comprising the steps of placing a plurality of electrical-activity transducers at spaced apart locations on the skull of a patient, repeatedly providing a sensory stimulus for activating the brain to produce EP responses at said transducers, averaging said responses to produce average responses for each transducer, processing said average responses to generate a time sequence of matrices, displaying said matrices as a time sequence of topographic maps of the skull, said matrices having elements defining discrete points of said maps, and displaying said topographic maps at a variable frame rate, maps corresponding to different portions of said average responses being displayed respectively at different selected frame rates.

73. A method for generating a topographic display of information on the electrical activity of the brain, said method including the steps of placing a plurality of electrical-activity transducers at spaced apart locations on the skull, processing responses of said transducers to generate a time sequence of matrices, each said matrix having elements representing the instantaneous amplitudes of said responses at various locations on the skull and there being a sufficient number of said matrices for a selected time period of actual brain activity for capturing onset of a transient event that occurs with a rapidity on the order of that of an epileptic spike, generating from said time sequence of matrices a running-average matrix which at any given time represents the current matrix averaged with a selected number of the matrices preceding it in time, displaying said matrices as a time sequence of topographic maps of the skull at a variable frame rate, each running-average matrix having elements defining discrete points of said maps, and selectably slowing the frame rate at which said topographic maps are displayed so as to permit observation of said transient event.

74. A method for generating a topographic display of information on the electrical activity of the brain, said method comprising the steps of placing a plurality of electrical-activity transducers at spaced apart locations on the skull of a patient to measure the EEG response at said locations, sampling the EEG responses during time intervals shorter than the anticipated interval between interruptions in the state of brain activity, computing, for each of said transducers, the Fourier transforms of the sampled EEG responses and computing from said Fourier transforms, for each of said transducers, the spectral energy contained in selected frequency bands, processing said computed spectral energy of said selected frequency bands to generate a plurality of matrices, one said matrix for each selected frequency band, said matrices having elements representing the spectral energy within the respective frequency band at one location on the skull, and displaying said matrices as topographic maps of the skull, said matrix elements forming discrete points of said maps.

75. A method for generating a topographic display of information on the electrical activity of the brain, said method comprising the steps of placing a plurality of electrical-activity transducers at spaced apart locations on the skull of a patient, processing electrical responses measured at said transducers, said processing means including means for generating one or more matrices, each matrix containing a plurality of elements, said elements representing information on the electrical activity of the brain at particular skull locations, processing at least two said matrices to generate a statistical comparison matrix said statistical comparison matrix having elements each of which representative of a statistical difference between the corresponding elements in said two matrices, and displaying said statistical comparison matrix as a topographic map of the skull, said matrix elements forming discrete points of said map.

76. A method for generating a topographic display of information on the electrical activity of the brain, said method comprising the steps of placing a plurality of electrical-activity transducers at spaced apart locations on the skull of a patient, statistically processing responses at said electrical-activity transducers to generate a coefficient-of-variance matrix, said matrix having elements each of which represents the normalized standard deviation of the responses at one skull location, the normalized standard deviation being the standard deviation divided by the mean, displaying said coefficient-of-variance matrix as a topographic map of the skull, thereby providing a map of the level of variation in brain activity.

77. A method for generating a topographic display of information on the electrical activity of the brain, said method comprising the steps of placing a plurality of electrical-activity transducers for placement at spaced apart locations on the skull of a patient, generating from responses measured at said transducers a time sequence of first matrices, each said first matrix having display elements representing the instantaneous response at various locations on said skull, generating by interpolation second matrices interspersed in said sequence of first matrices, said second matrices having elements representing the approximate response at instants of time intermediate the instants of time associated with said first matrices, displaying said first matrices and said interspersed second matrices as a time sequence of topographic maps of the skull, said matrix elements forming discrete points of said maps, said second matrices enhancing the visual smoothness of the transitions over time between said first matrices.

78. A method for generating a topographic display of information on the electrical activity of the brain, said method comprising the steps of placing a plurality of electrical-activity transducers at spaced apart locations on the skull of a patient, generating one or more matrices from responses measured at said transducers, each matrix having elements representing information on the electrical activity of the brain at one location on the skull, displaying said one or more matrices as topographic maps of the skull, said matrix elements forming discrete points of said maps, previewing said transducer responses or processed versions thereof, said previewing including at least two of the following steps tagging a response with information on its waveform quality, including an indication of whether the response should be used in later processing, eliminating a response from further processing at the discretion of the operator, automatically eliminating a response from further processing if a portion thereof exceeds a predetermined threshold, smoothing a response to eliminate undesired high frequency components, adjusting a zero baseline of a response, said zero baseline having been previously set automatically eliminating selected portions of a response from further processing, and displaying in numerical form the value of a response at a point in time selected by the operator.

79. A method for generating a topographic display of information on the electrical activity of the brain, said method comprising the steps of placing a plurality of electrical-activity transducers at spaced apart locations on the skull of a patient, sampling responses measured at said transducers and storing the sampled data as a series of data matrices, one matrix for each sampling time, selectively viewing the sampled data corresponding to a single transducer as a plot of transducer output versus time, adjusting portions of said selectively viewed data or eliminating said data from further processing, processing said data matrices to generate one or more processed matrices said one or more processed matrices having elements each corresponding to one transducer location, expanding the number of elements in said one or more processed matrices to provide elements corresponding to skull locations intermediate said transducer locations, providing a video monitor capable of generating a matrix of grey tones for displaying said expanded matrices as topographic maps of the skull, said expanded matrix elements defining the grey tones of discrete points on said maps.

80. A method for generating a topographic display of information on the electrical activity of the brain, said method comprising the steps of placing a plurality of electrical-activity transducers at spaced apart locations on the skull of a patient, processing responses measured at said transducers to generate one or more matrices, each matrix having elements representing information on brain activity at different skull locations, displaying one or more said matrices as topographic maps of the skull, said matrix elements forming discrete points of said maps, providing a video monitor which generates a visible grey tone at each said discrete point, said tone being variable from a maximum tone to a minimum tone, and scaling said matrix elements to the available tones.

81. The method of claim 80 wherein said providing step comprises providing a said video monitor which generates a zero tone intermediate said maximum and minimum tone, and said scaling step comprises at least two of the following steps scaling the maximum matrix element to the maximum tone and the minimum matrix element to the minimum tone and linearly interpolating inbetween, scaling the maximum matrix element to the maximum tone and the minimum matrix element to the zero tone and linearly interpolating in between, scaling the maximum matrix element to an operator supplied tone, scaling the minimum matrix element to an operator supplied tone, excluding from the scaling operation selected unusually high or low valued matrix elements and assigning to matrix elements that fall outside the available tone range the closer of the maximum or minimum tone.

82. A method for generating a topographic display of information on the electrical activity of the brain, said method comprising the steps of placing a plurality of electrical-activity transducers at spaced apart locations on the skull of a patient, processing responses measured at said transducers to generate one or more matrices, each matrix having elements representing information on brain activity at different skull locations, displaying said one or more matrices as a topographic map of the skull, said matrix elements forming discrete points of said map, providing a video monitor which generates a tone at each said discrete point, said tone varying from a maximum tone to a minimum tone, normalizing said matrix elements to a selected value, and scaling said matrix elements to the available tones, said scaling means including means for assigning a selected tone to said selected normalization value.

* * * * *